(12) United States Patent
Hong et al.

(10) Patent No.: US 9,017,829 B2
(45) Date of Patent: Apr. 28, 2015

(54) PHENANTHROCARBAZOLE COMPOUND, AND ORGANIC ELECTROLUMINESCENT DEVICE USING SAME

(75) Inventors: Jin-Seok Hong, Suwon-si (KR); Eun Jung Lee, Seoul (KR); Shin Han Kim, Yongin-si (KR); Kyoung-Soo Kim, Daejeon (KR)

(73) Assignee: Doosan Corporation, Seoul (KR)

( * ) Notice: Subject to any disclaimer, the term of this patent is extended or adjusted under 35 U.S.C. 154(b) by 365 days.

(21) Appl. No.: 13/696,241

(22) PCT Filed: May 6, 2011

(86) PCT No.: PCT/KR2011/003412
§ 371 (c)(1),
(2), (4) Date: Nov. 5, 2012

(87) PCT Pub. No.: WO2011/139125
PCT Pub. Date: Nov. 10, 2011

(65) Prior Publication Data
US 2013/0048975 A1    Feb. 28, 2013

(30) Foreign Application Priority Data
May 6, 2010    (KR) .................. 10-2010-0042577

(51) Int. Cl.
| H01L 51/54 | (2006.01) |
| C09K 11/06 | (2006.01) |
| C07D 209/80 | (2006.01) |
| C07D 401/04 | (2006.01) |
| C07D 403/04 | (2006.01) |
| C07D 409/10 | (2006.01) |
| H01L 51/00 | (2006.01) |
| H05B 33/14 | (2006.01) |

(52) U.S. Cl.
CPC .............. *C09K 11/06* (2013.01); *C07D 209/80* (2013.01); *C07D 401/04* (2013.01); *C07D 403/04* (2013.01); *C07D 409/10* (2013.01); *H01L 51/0072* (2013.01); *H05B 33/14* (2013.01); *C09K 2211/1029* (2013.01); *C09K 2211/1044* (2013.01); *C09K 2211/1059* (2013.01); *C09K 2211/1092* (2013.01); *H01L 51/0085* (2013.01)

(58) Field of Classification Search
None
See application file for complete search history.

(56) References Cited

U.S. PATENT DOCUMENTS

| 2004/0076853 A1* | 4/2004 | Jarikov ..................... 428/690 |
| 2008/0124455 A1 | 5/2008 | Shin et al. |
| 2009/0295276 A1 | 12/2009 | Asari et al. |
| 2011/0210318 A1 | 9/2011 | Bae et al. |

FOREIGN PATENT DOCUMENTS

| JP | 2003-055276 A | 2/2003 |
| KR | 10-2008-0047209 A | 5/2008 |
| WO | 2007/063796 A1 | 6/2007 |
| WO | 2010/021524 A2 | 2/2010 |

OTHER PUBLICATIONS

Saa' et al., Synthesis of Carbazoles by dehydro Diels-Adder reactions of ynamides, 2008, Tetrahedron, vol. 64, pp. 3674-3686.*

* cited by examiner

*Primary Examiner* — Gregory Clark
(74) *Attorney, Agent, or Firm* — Sughrue Mion, PLLC

(57) ABSTRACT

The present invention relates to a material for an organic electroluminescent device, including a phenanthrocarbazole-based compound having a specific structure, and an organic electroluminescent device including the same. More specifically, the phenanthrocarbazole-based compound is applied as a material for a phosphorescent and fluorescent organic electroluminescent device, thereby providing an organic light emitting device with improved light emitting efficiency, luminance, thermal stability, driving voltage, lifetime and the like.

6 Claims, No Drawings

PHENANTHROCARBAZOLE COMPOUND, AND ORGANIC ELECTROLUMINESCENT DEVICE USING SAME

TECHNICAL FIELD

The present invention relates to a phenanthrocarbazole-based material for an organic electroluminescent device, having a specific structure, and an organic electroluminescent device comprising the material in one or more organic layers to improve various properties such as light emitting efficiency, luminance, thermal stability, driving voltage, and lifetime.

BACKGROUND ART

In a study on an organic electroluminescent (EL) device (hereinafter, referred to as 'organic EL device'), which has continued from an organic thin film light emission observation by Bernanose in 1950 to blue electroluminescence using an anthracene single crystal in 1965, an organic EL device having a lamination structure including functional layers of a hole layer and a light emitting layer was proposed by Tang in 1987. Subsequently, the organic EL device has been developed in a form of introduction of a specific organic layer into a device and a specific material used therein has been developed in order to manufacture the organic EL device having high efficiency and long lifetime.

The organic EL device is formed of an ITO (indium tin oxide) substrate, an anode, a hole injection layer selectively receiving holes from an anode, a hole transport layer selectively transporting the holes, a light emitting layer emitting light by re-bonding the holes and the electrons, an electron transport layer selectively transporting the electrons, an electron injection layer selectively receiving the electrons from a cathode, and the cathode. As described above, the reason why the organic EL device is manufactured to have multilayers is because moving speeds of the holes and the electrons are different from each other, and if the appropriate hole injection layer, hole transport layer, electron transport layer, and electron injection layer are manufactured, the holes and the electrons can be efficiently transported, and a balance of the holes and the electrons in the device may be ensured, thus increasing light emitting efficiency. The electrons injected into the electron injection layer and the holes transported to the hole injection layer are re-bonded in the light emitting layer to form an exciton, light emission by falling from a singlet excited state to a bottom state is called fluorescence and light emission by falling from a triplet excited state to a bottom state is called phosphorescence. Theoretically, when carriers are re-bonded in the light emitting layer to generate the exciton, a ratio of the singlet exciton and the triplet exciton may become 1:3, and in the case where phosphorescence is used, internal quantum efficiency may be 100%.

Meanwhile, generally, a carbazole-based compound such as CBP (4,4-dicarbazolybiphenyl) is used as a phosphorescent host material, and a metal complex compound including heavy atoms such as Ir and Pt is extensively used as a phosphorescent dopant material. However, in the case of CBP that is the currently used phosphorescent host material, there are problems in that a glass transition temperature (Tg) is about 110° C., which is low, and lifetime of the organic EL device is about 150 hours, which is very short, because crystallization easily occurs in the device.

DISCLOSURE

Technical Problem

The present invention has been made to solve the above-mentioned problems and intends to provide a material of an organic light emitting device, having improved various properties such as light emitting efficiency, luminance, thermal stability, driving voltage, and lifetime, and an organic EL device using the material.

Technical Solution

In accordance with a first aspect of the present invention, there are provided a compound represented by the following Chemical Formula 1, a compound represented by Chemical Formula 2, a compound represented by Chemical Formula 3, a compound represented by Chemical Formula 4, and preferably a phenanthrocarbazole compound-based material for an organic electroluminescent device.

[Chemical Formula 1]

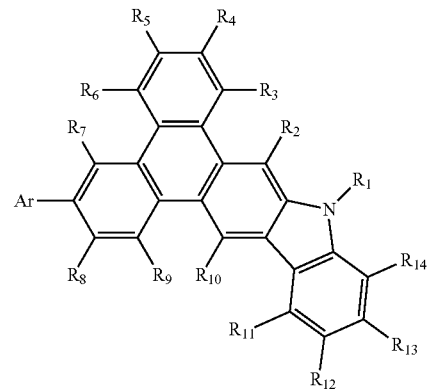

wherein,

Ar is an aromatic hydrocarbon ring group or an aromatic amine ring group, and selected from the group consisting of benzene, naphthalene, biphenyl, anthracene, phenanthrene, pyrene, perylene, triphenylene, and triphenyl amine, $R_1$ to $R_{14}$ are each independently selected from the group consisting of hydrogen, deuterium, a halogen atom, an alkyl group having 1 to 40 carbon atoms, a hetero-ring group having 3 to 40 nucleus atoms, an alkoxy group having 1 to 40 carbon atoms, an aromatic hydrocarbon group having 6 to 40 nucleus carbon atoms, an aryloxy group having 6 to 40 carbon atoms, an arylalkyl group having 7 to 40 carbon atoms, an alkenyl group having 2 to 40 carbon atoms, an alkylamino group having 1 to 40 carbon atoms, an arylamino group having 6 to 40 carbon atoms, an arylalkylamino group having 7 to 40 carbon atoms, an alkylsilyl group having 3 to 20 carbon atoms, an arylsilyl group having 8 to 40 carbon atoms, a ketoaryl group having 7 to 40 carbon atoms, a halogenated alkyl group having 1 to 40 carbon atoms, and a cyano group, and $R_1$ to $R_{14}$ may each independently bind with adjacent substituents, or the substituents introduced to Ar may each independently bind with adjacent substituents to form a saturated or unsaturated ring structure (cyclic structure).

[Chemical Formula 2]

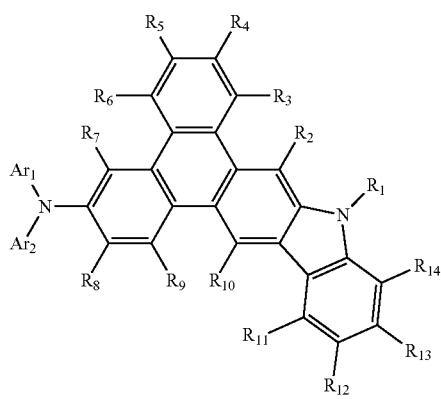

wherein, $Ar_1$ and $Ar_2$ may be the same as or different from each other, and are each independently selected from the group consisting of benzene, naphthalene, biphenyl, anthracene, phenanthrene, pyrene, perylene, and triphenylene, and $Ar_1$ and $Ar_2$ may each independently bind with the adjacent substituents to form a saturated or unsaturated ring structure, $R_1$ to $R_{14}$ are the same as definitions of Chemical Formula 1; and $R_1$ to $R_4$, $R_5$ to $R_8$, $R_9$ to $R_{12}$, and $R_{13}$ to $R_{14}$ may each independently bind with adjacent substituents, or $R_{12}$ and $R_{13}$ may be bonded to each other to form a saturated or unsaturated ring structure (cyclic structure).

[Chemical Formula 3]

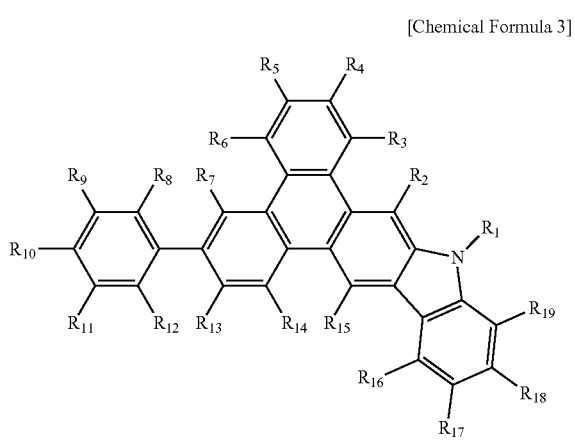

wherein, $R_1$ to $R_{19}$ are the same as definitions of $R_1$ to $R_{14}$ of Chemical Formula 1; and $R_7$ to $R_8$, $R_8$ to $R_{13}$, and $R_8$ to $R_{12}$ may each independently bind with adjacent substituents to form a saturated or unsaturated ring structure (cyclic structure).

[Chemical Formula 4]

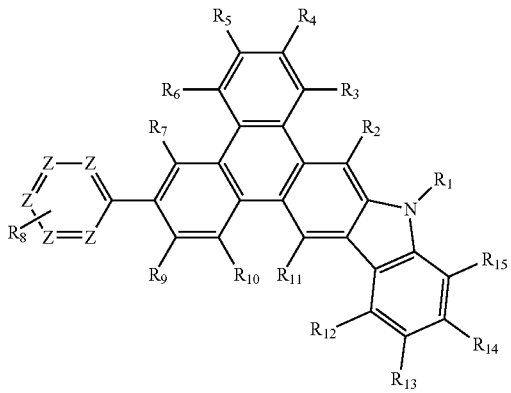

wherein, $R_1$ to $R_{15}$ are each independently the same as definitions of $R_1$ to $R_{14}$ of Chemical Formula 1; and a plurality of Zs are each independent and may be the same as or different from each other even though a plurality of Zs are identically represented, and at least one of a plurality of Zs is a nitrogen atom and others are a carbon atom.

In accordance with a second aspect of the present invention, an organic light emitting device comprises: an anode; a cathode; and one or more organic layers interposed between the anode and the cathode, wherein at least one of the organic layers comprises one or more compounds selected from the group consisting of a compound represented by Chemical Formula 1, a compound represented by the following Chemical Formula 2, a compound represented by the following Chemical Formula 3, and a compound represented by the following Chemical Formula 4.

In this case, the compounds represented by Chemical Formulas 1 to 4 may be used in one or more selected from the group consisting of a light emitting layer, a hole injection layer, and a hole transport layer.

Advantageous Effects

In the present invention, various properties such as light emitting efficiency, luminance, thermal stability, driving voltage, and lifetime of an organic electroluminescent device can be improved by applying a predetermined material for an organic electroluminescent device having a symmetric or asymmetric molecular structure to a phosphorescent organic electroluminescent device, preferably a hole transport layer material, an electron transport layer material, or a phosphorescent light emitting layer, and particularly a green or red host material.

BEST MODE

The present invention provides a phenanthrocarbazole compound having a predetermined structure having a molecular weight that is higher than that of a material for a known organic light emitting device having a wide energy band gap [for example, N4,N4'-di(naphthalen-1-yl)-N4,N4'-diphenylbiphenyl-4,4'-diamine (hereinafter, referred to as "α-NPB") and 4,4-dicarbazolylbiphenyl (hereinafter, referred to as "CBP")].

As the molecular weights of compounds represented by Chemical Formulas 1 to 4 are increased, a glass transition temperature (Tg) may be improved to ensure thermal stability, thus improving durability and lifetime. Further, a steric hindrance may occur due to the asymmetric molecular structure to disturb crystallinity, accordingly, excellent performance may be exhibited in terms of lifetime.

In the case where the compound is adopted as a hole transport layer and blue, green and/or red phosphorescent host material or fluorescent host material of the organic electroluminescent device, performance may be largely improved in terms of efficiency and lifetime as compared to α-NPB and CBP. Accordingly, the compound according to the present invention represented by Chemical Formula 1 and preferably Chemical Formulas 1 to 4 may largely contribute to improving performance and lifetime of the organic electroluminescent device, and particularly, improvement in device lifetime largely affects maximization of performance in a full-color organic light emitting panel.

The following Chemical Formulas are representative examples of the compounds represented by Chemical Formulas 1 to 4 of the present invention, but the compounds represented by Chemical Formulas 1 to 4 of the present invention are not limited to the following examples.

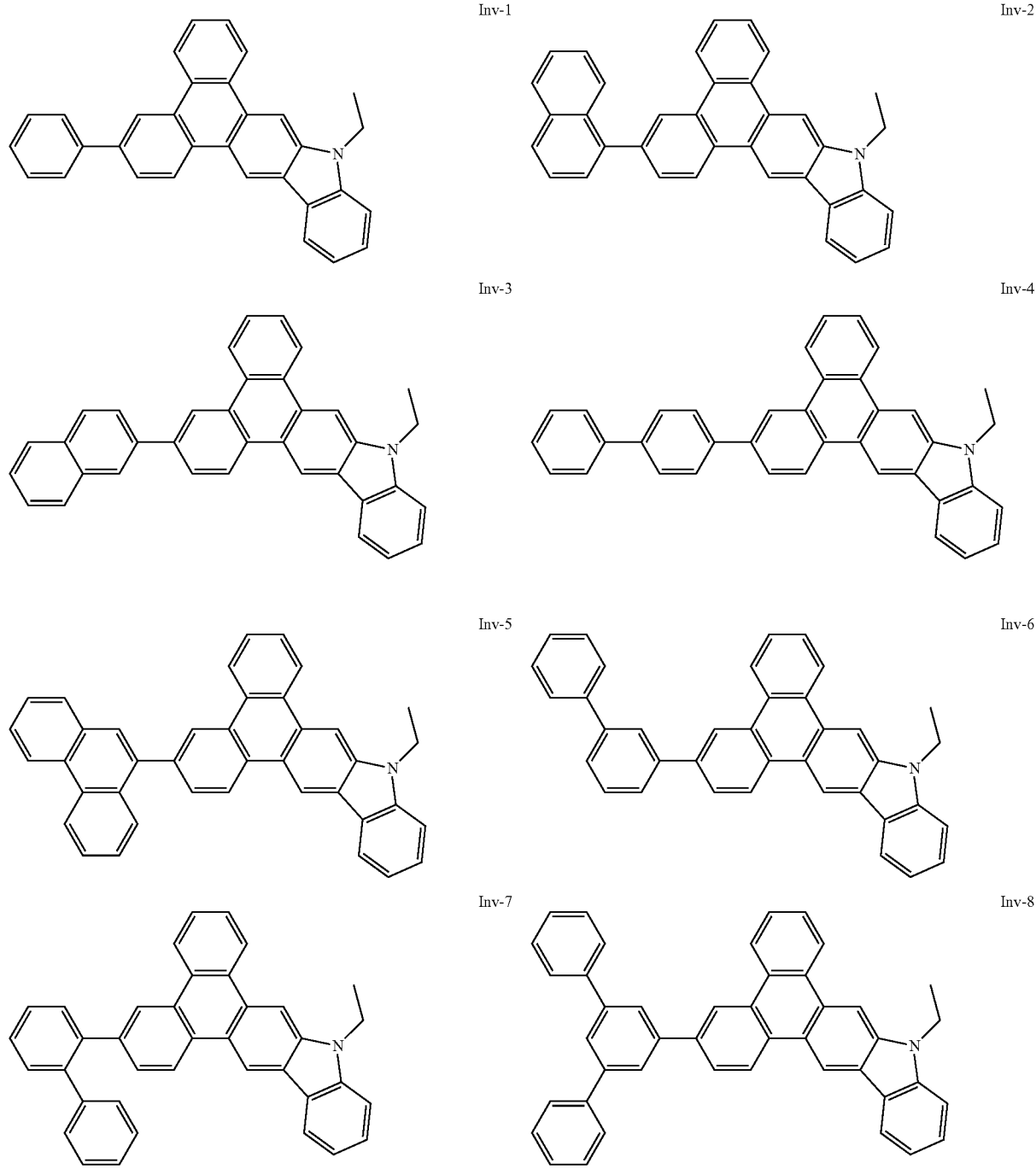

-continued
Inv-9
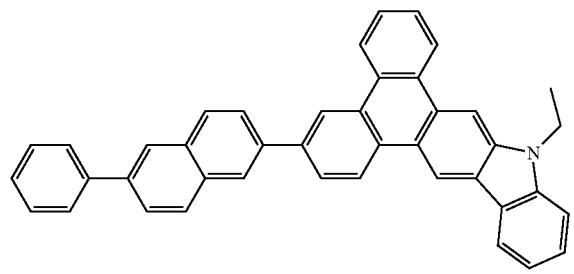
Inv-10
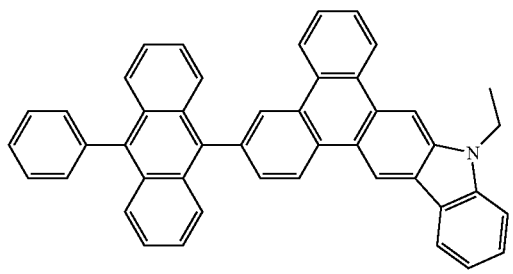
Inv-11
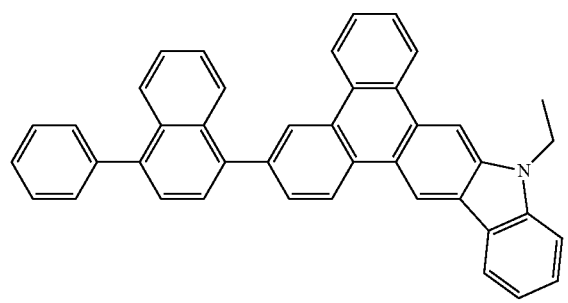
Inv-12
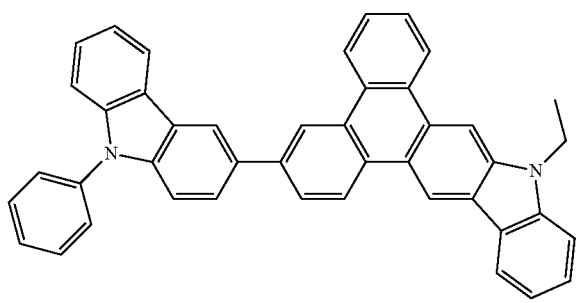
Inv-13
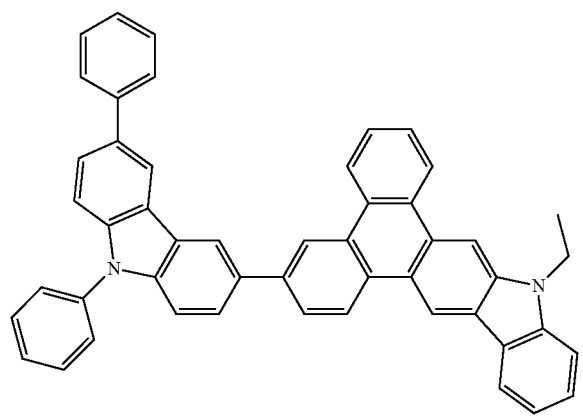
Inv-14
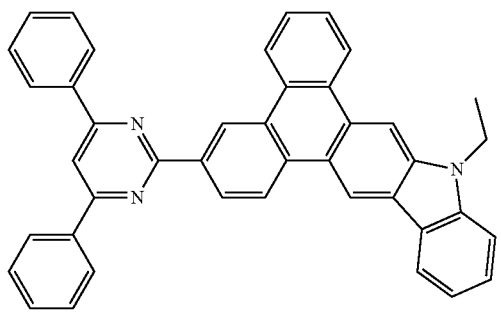
Inv-15
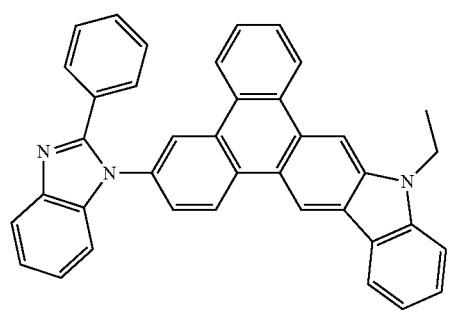
Inv-16
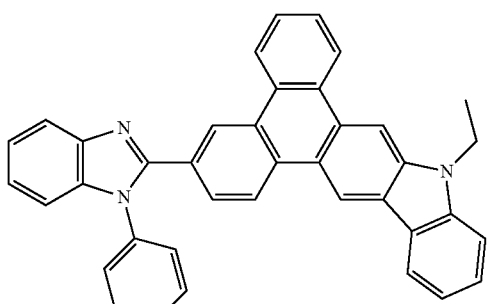

-continued
Inv-17
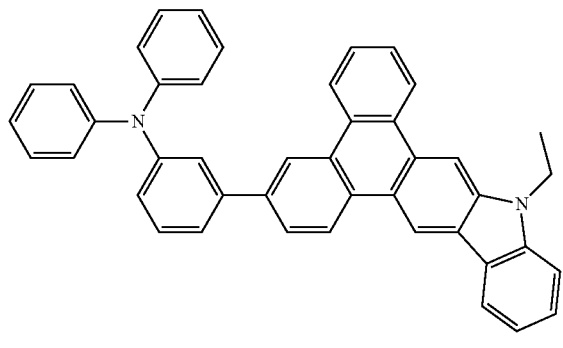
Inv-18
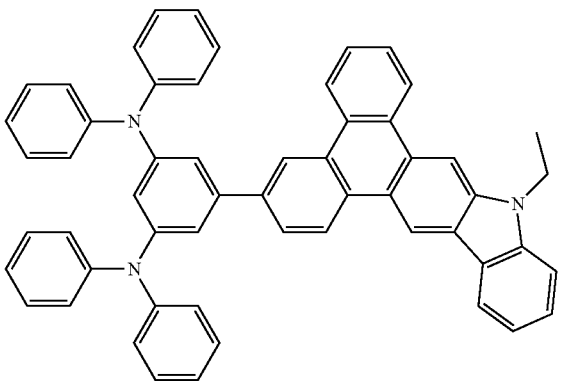
Inv-19
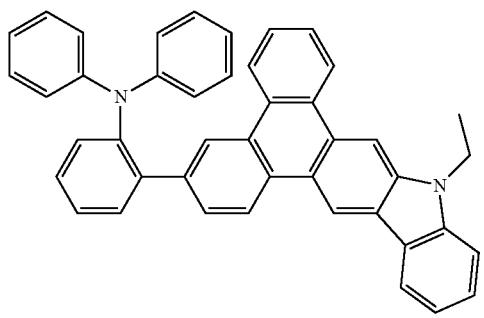
Inv-20
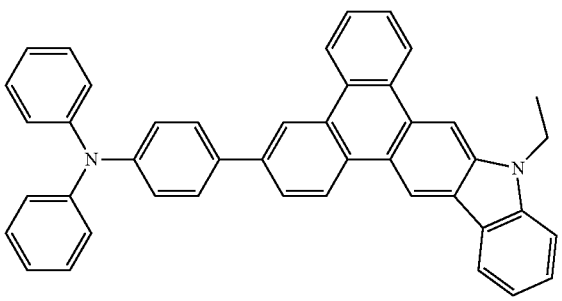
Inv-21
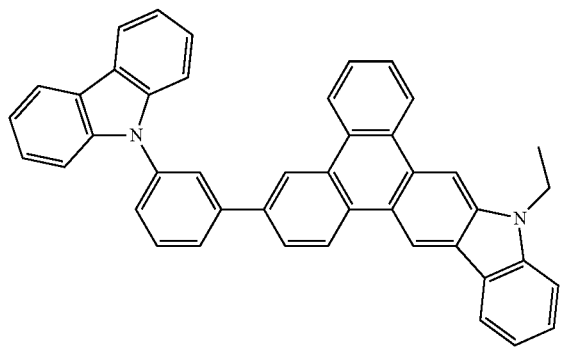
Inv-22
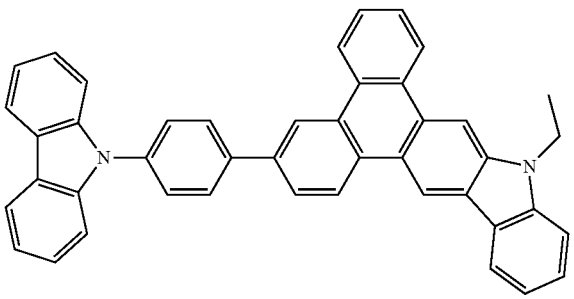
Inv-23
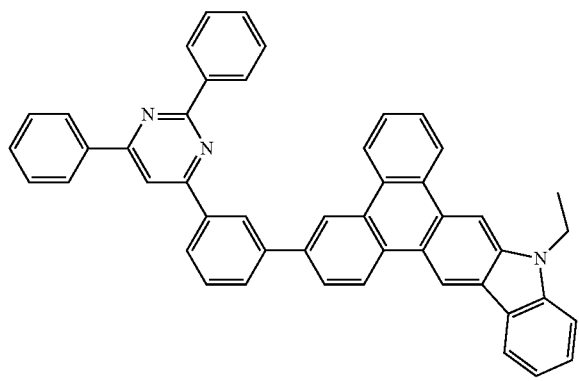
Inv-24
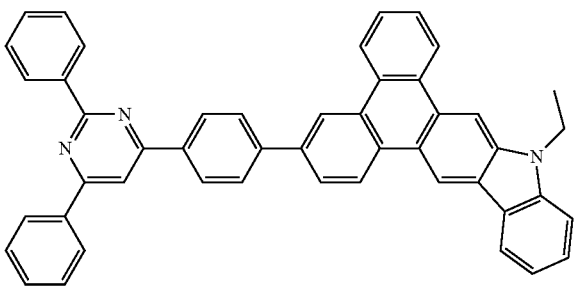

-continued
Inv-25
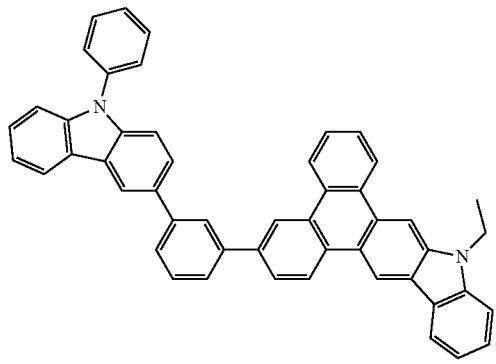
Inv-26
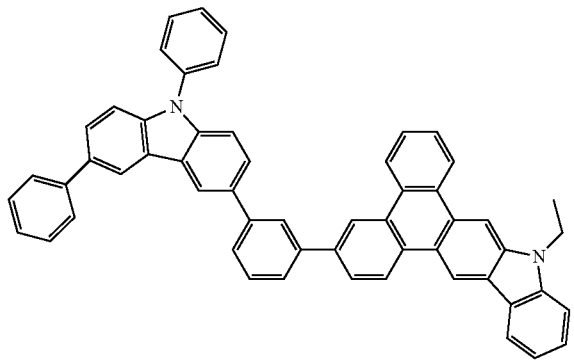
Inv-27
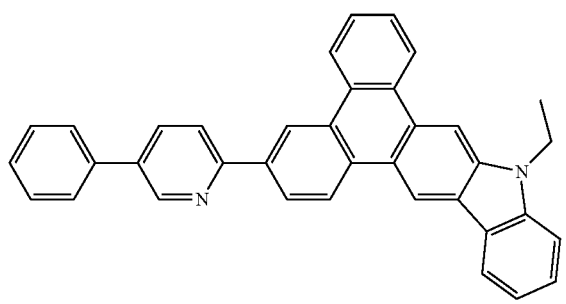
Inv-28
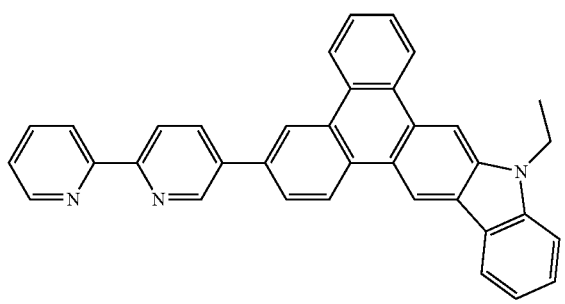
Inv-29
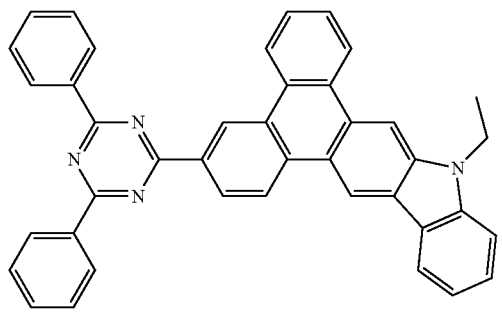
Inv-30
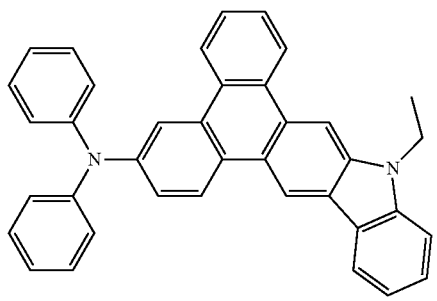
Inv-31
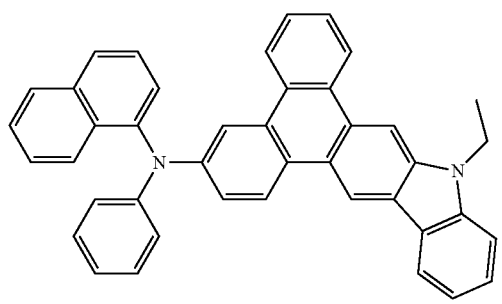
Inv-32
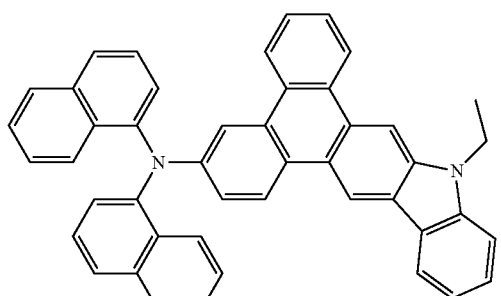
Inv-33
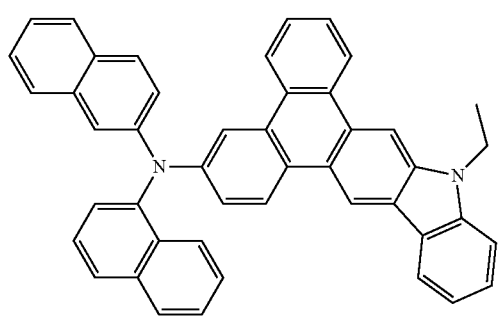
Inv-34
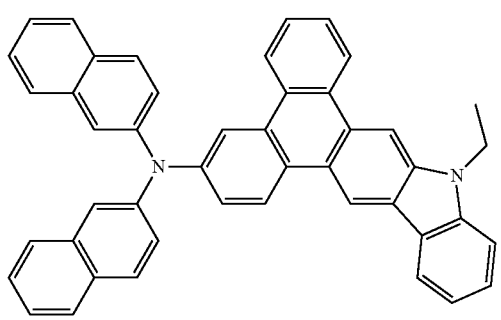

-continued
Inv-35
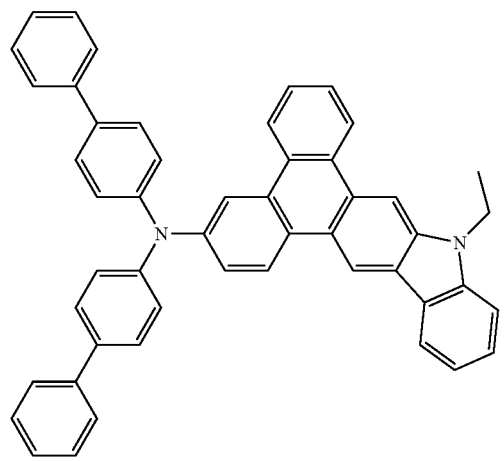
Inv-36
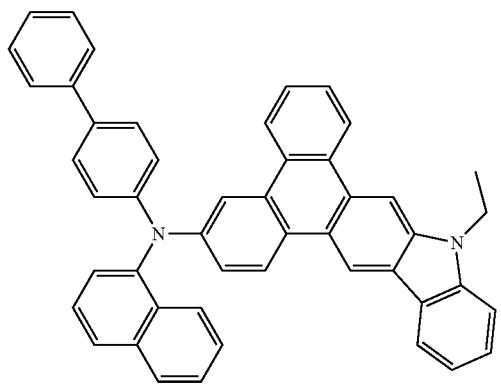
Inv-37
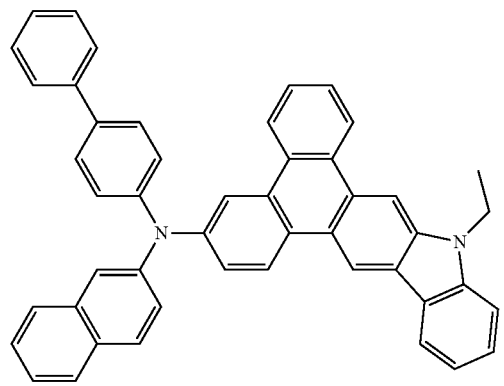
Inv-38
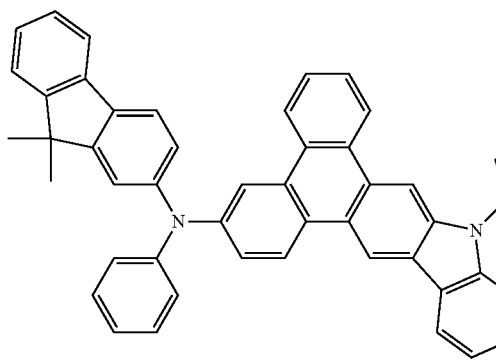
Inv-39
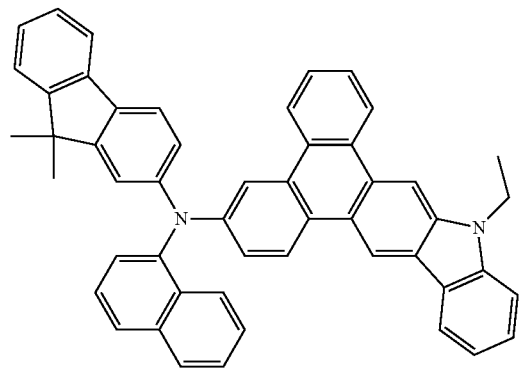
Inv-40
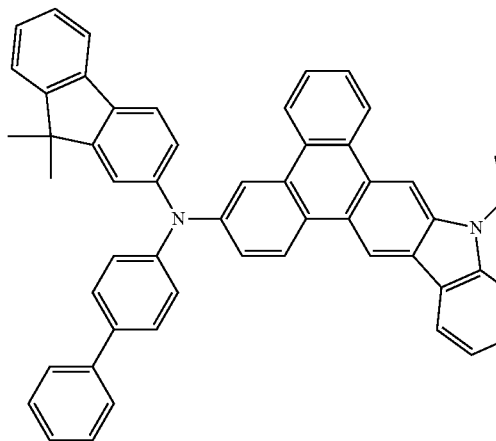
Inv-41
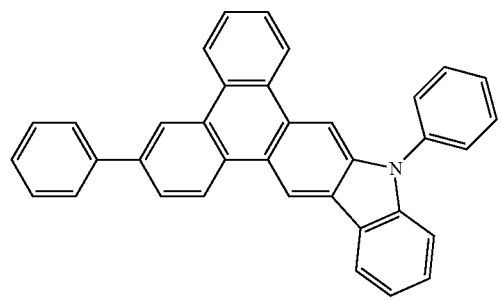
Inv-42
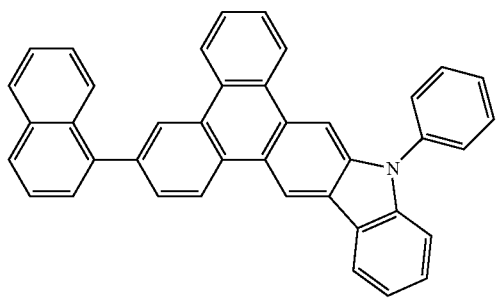

-continued
Inv-43
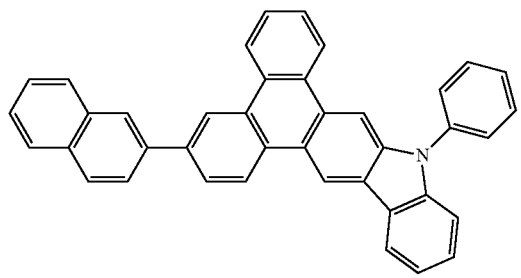
Inv-44
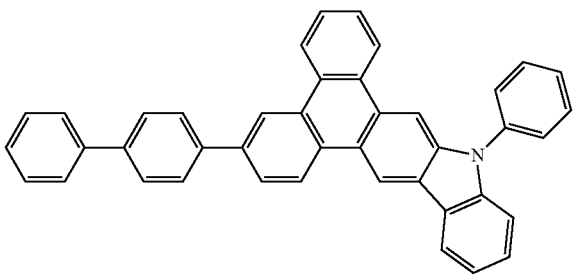
Inv-45
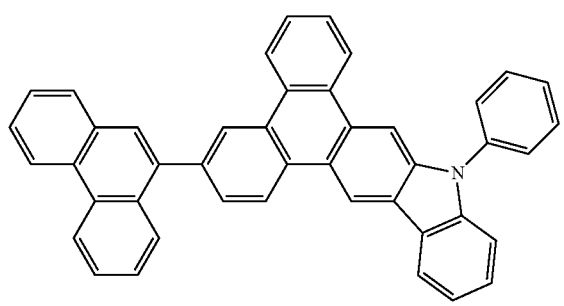
Inv-46
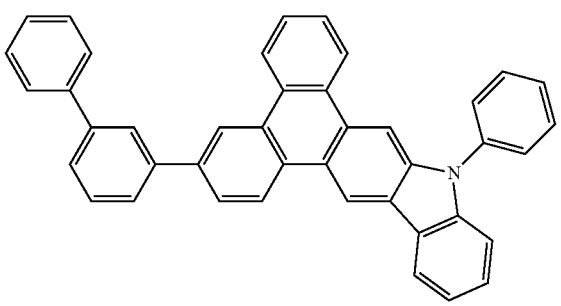
Inv-47
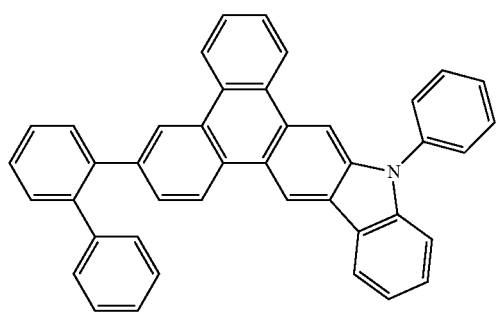
Inv-48
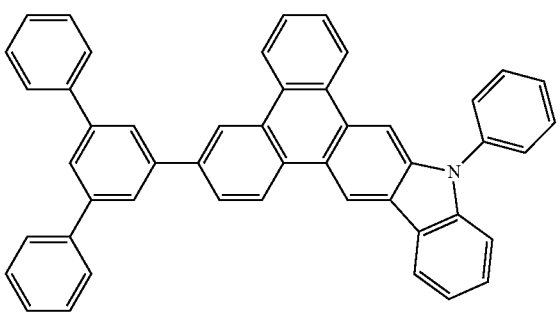
Inv-49
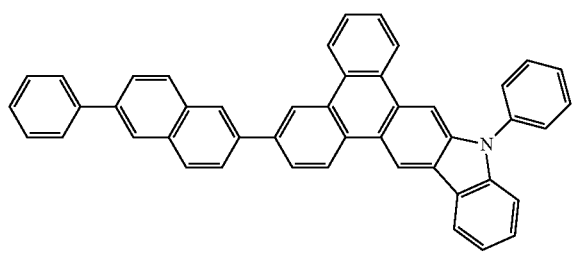
Inv-50
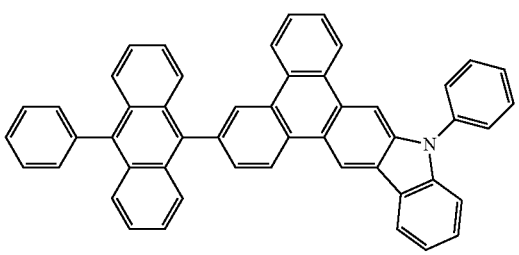
Inv-51
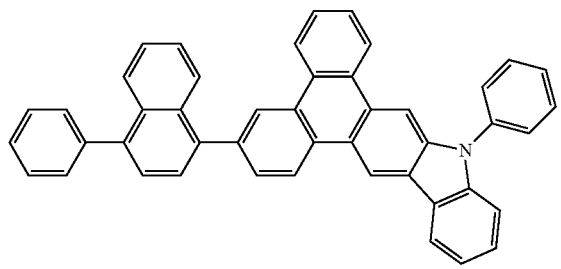
Inv-52
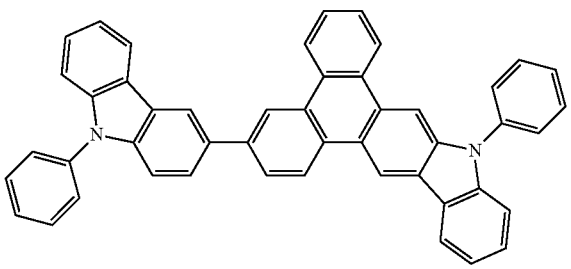

-continued
Inv-53
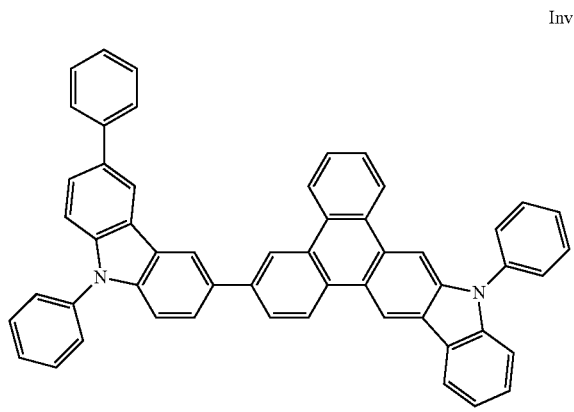
Inv-54
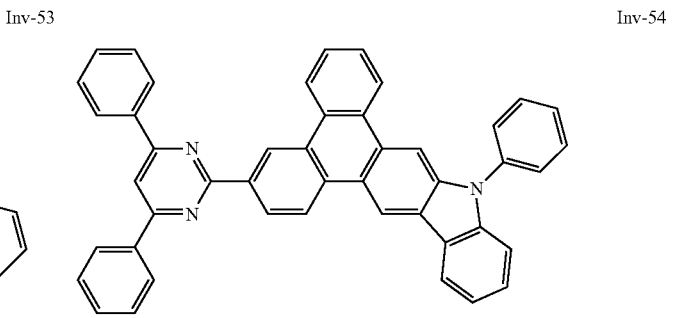
Inv-55
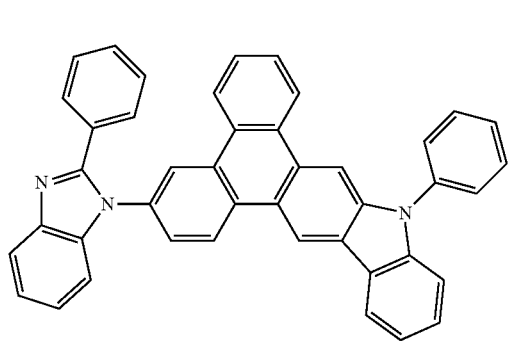
Inv-56
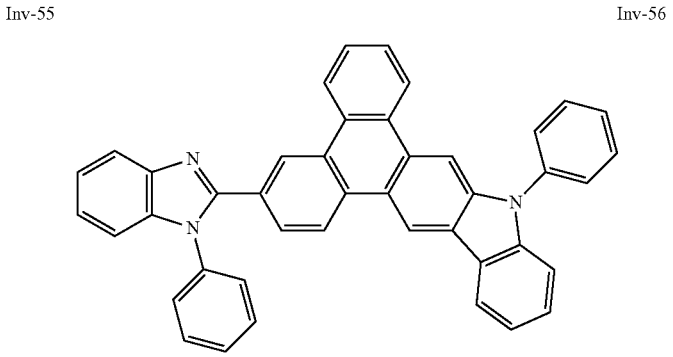
Inv-57
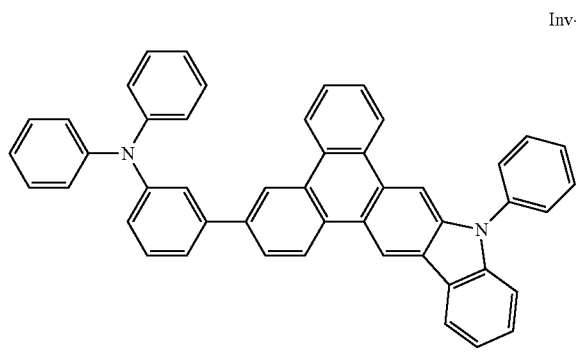
Inv-58
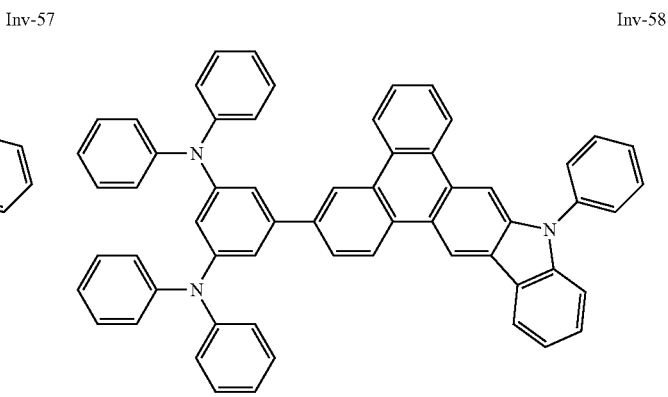
Inv-59
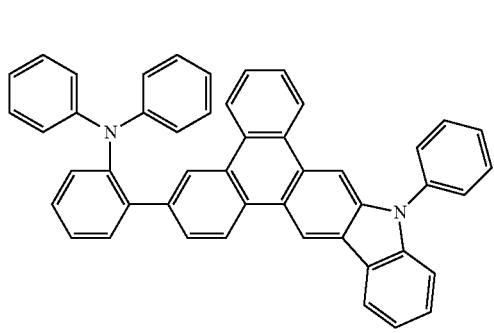
Inv-60
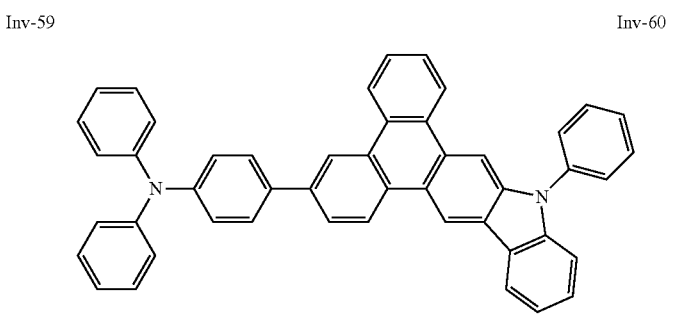

-continued
Inv-61
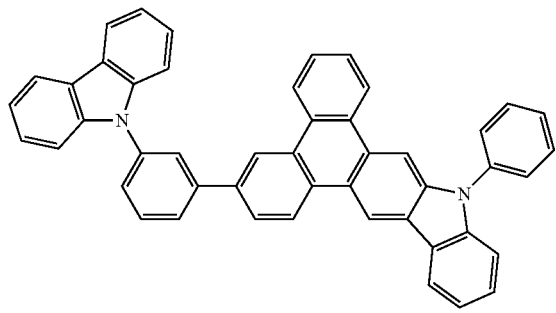
Inv-62
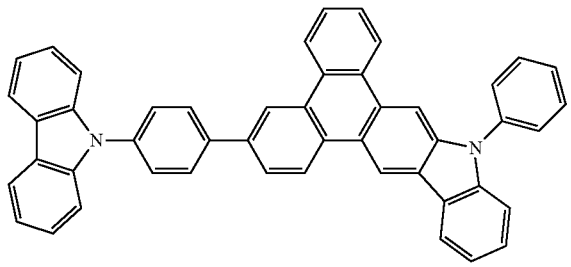
Inv-63
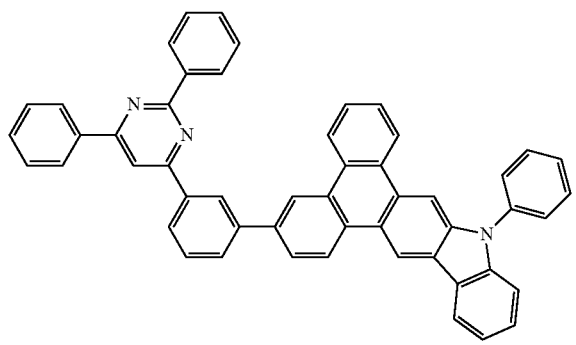
Inv-64
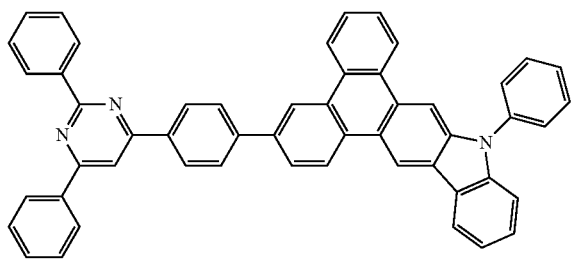
Inv-65
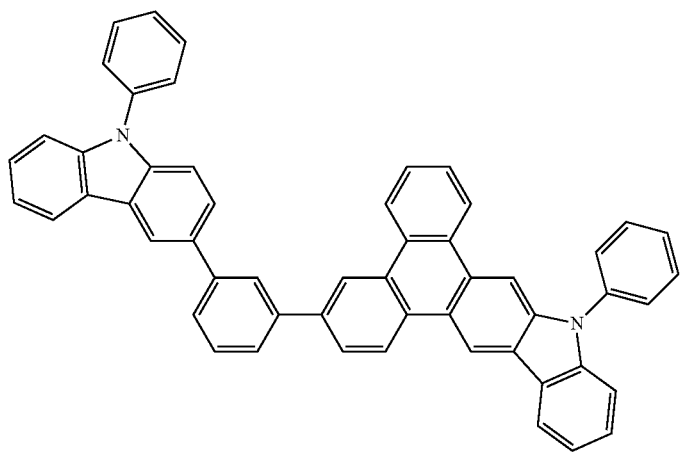
Inv-66
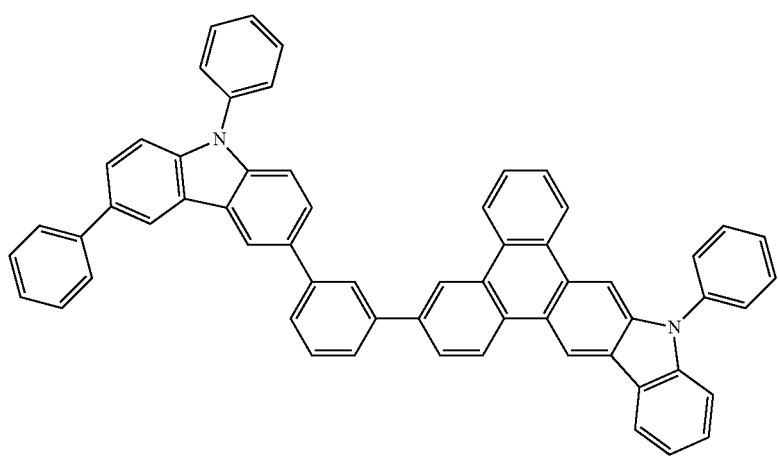

Inv-67
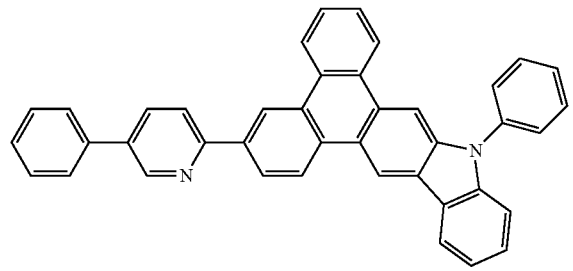
Inv-68
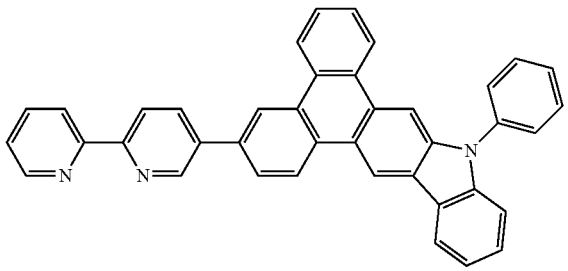
Inv-69
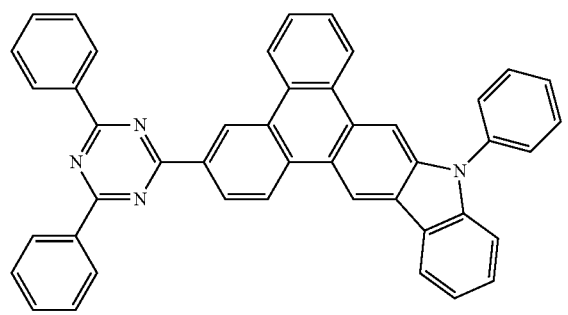
Inv-70
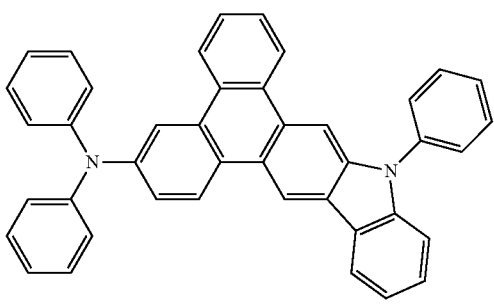
Inv-71
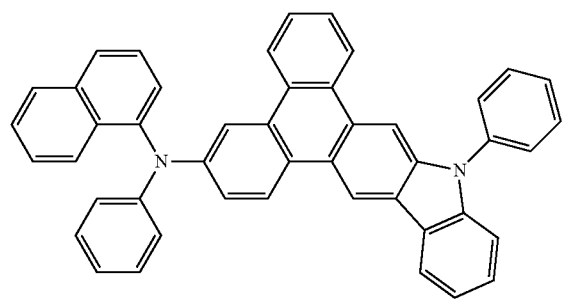
Inv-72
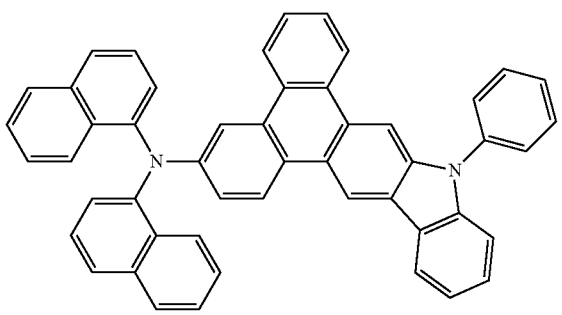
Inv-73
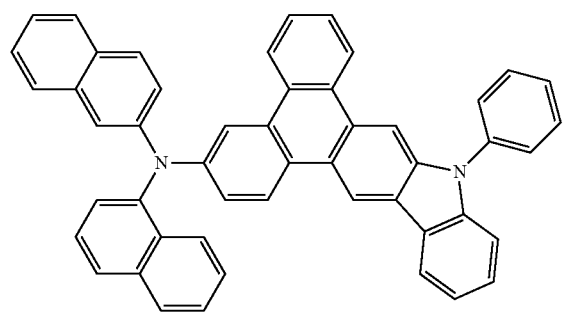
Inv-74
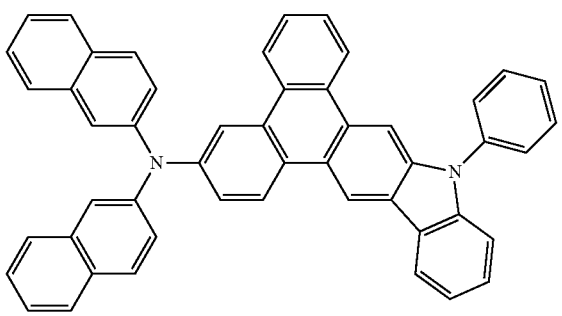

-continued
Inv-75
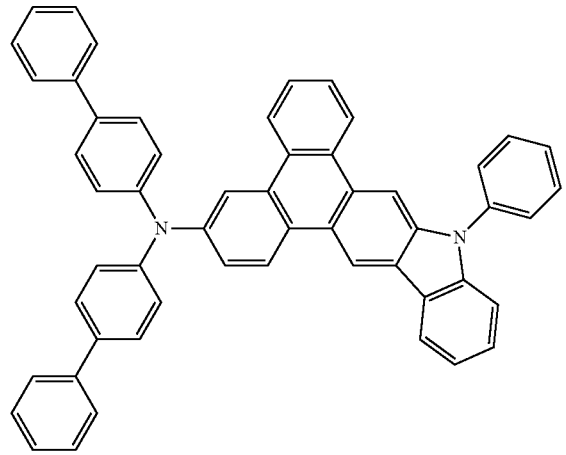
Inv-76
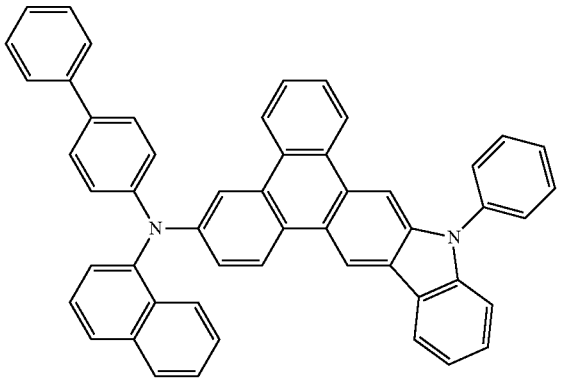
Inv-77
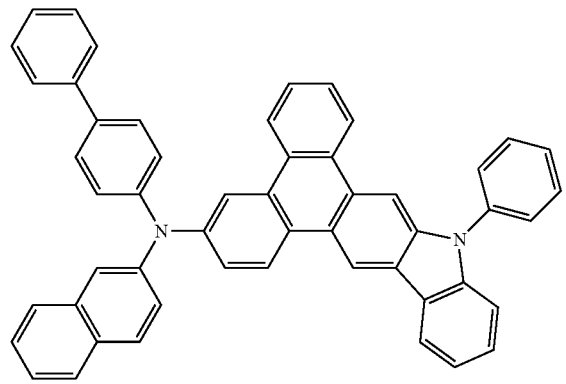
Inv-78
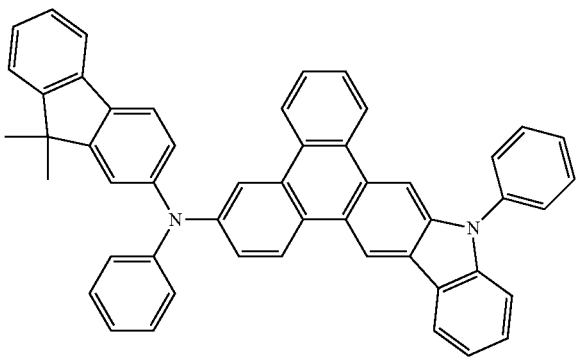
Inv-79
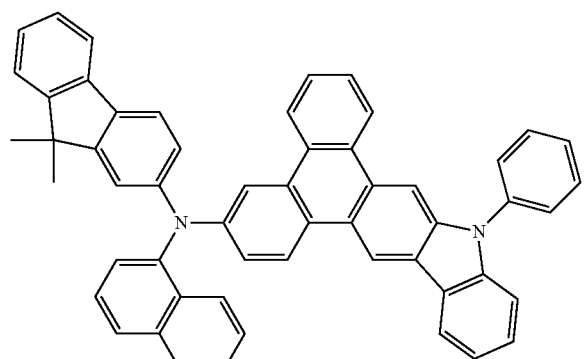
Inv-80
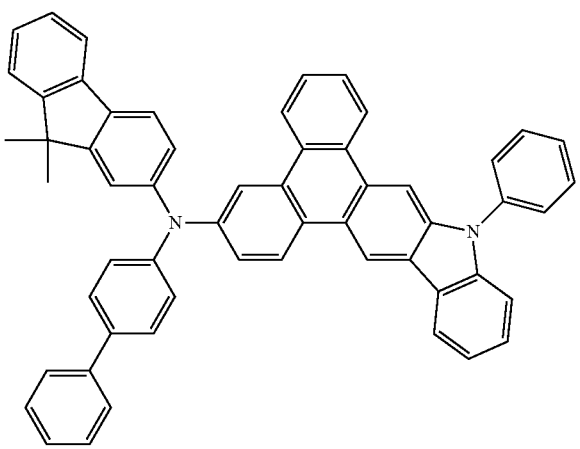

-continued
Inv-81
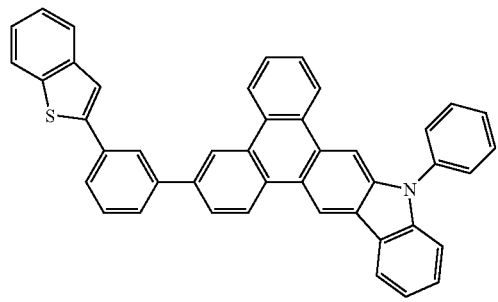
Inv-82
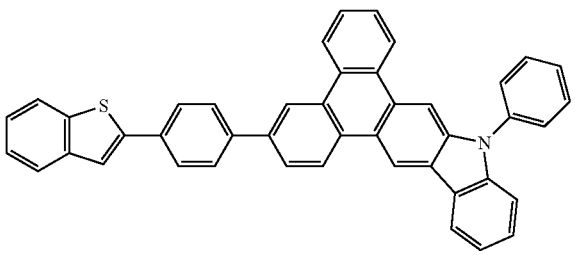
Inv-83
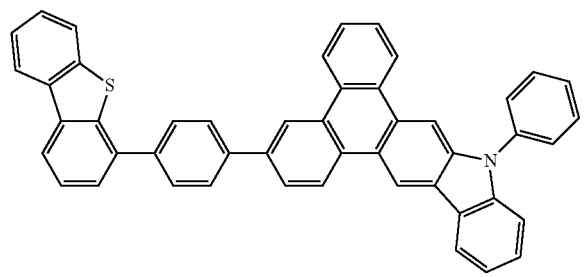
Inv-84
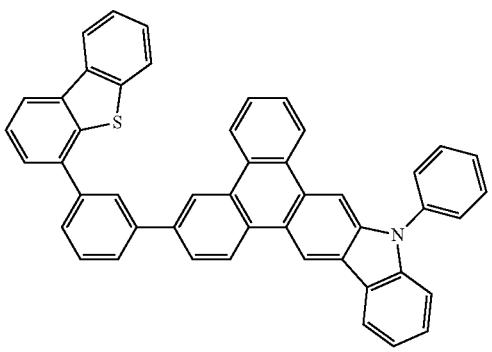
Inv-85
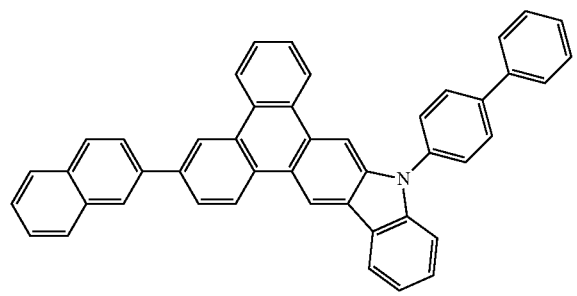
Inv-86
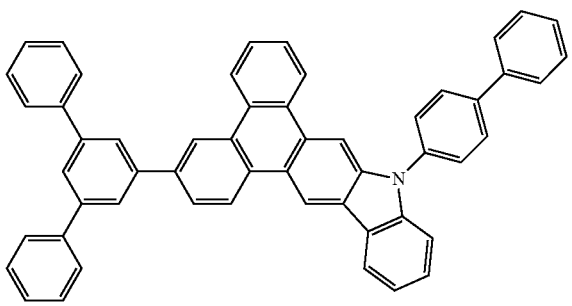
Inv-87
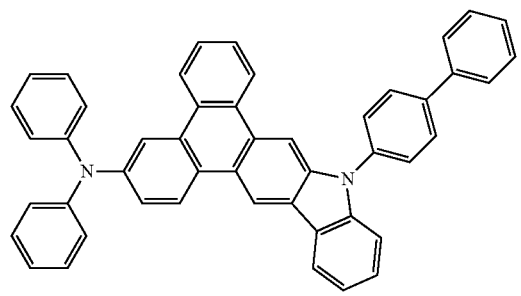
Inv-88
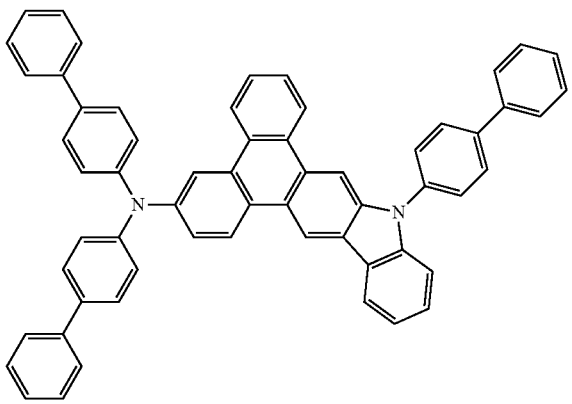

-continued

Inv-89
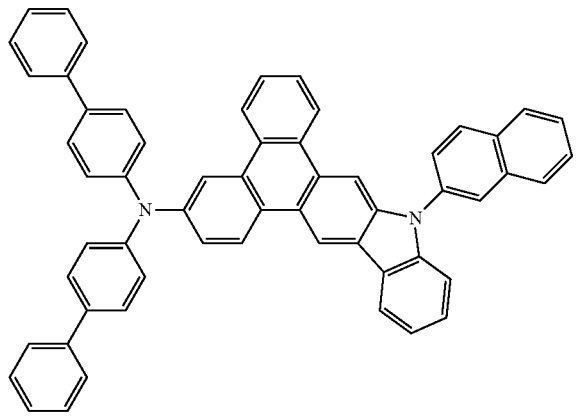

Inv-90
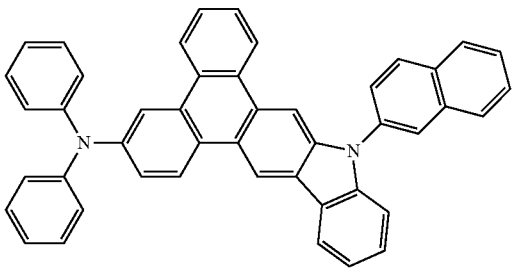

Inv-91
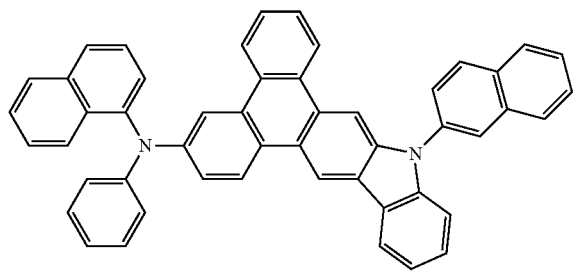

Inv-92
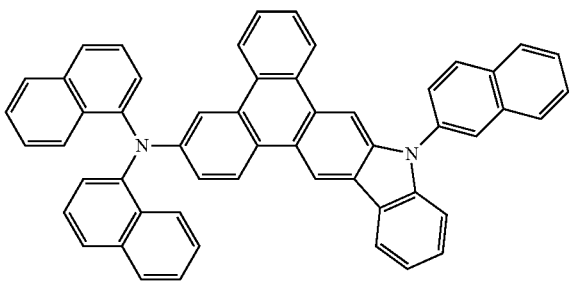

The compounds represented by Chemical Formulas 1 to 4 of the present invention may be synthesized according to a general synthesis method (see Chem. Rev., 60:313 (1960); J. Chem. SOC. 4482 (1955); Chem. Rev. 95: 2457 (1995)). A detailed synthesis procedure of the compound of the present invention will be specifically described in Synthetic Examples as described below.

Another aspect of the present invention relates to an organic electroluminescent device comprising the compound represented by Chemical Formulas 1 to 4 according to the present invention.

Specifically, the present invention is an organic electroluminescent device comprising an anode; a cathode; and one or more organic layers interposed between the anode and the cathode, wherein at least one of one or more organic layers comprises the compound represented by Chemical Formulas 1 to 4.

The compounds of Chemical Formula 1 to Chemical Formula 4 may be included alone or in combination.

The organic layer comprising the compound represented by Chemical Formulas 1 to 4 of the present invention may be one or more of a hole injection layer, a hole transport layer, and a light emitting layer. Preferably, the compounds represented by Chemical Formulas 1 to 4 may be included as materials of the hole injection layer and the hole transport layer in the organic EL device, and in this case, the organic EL device may maximize hole injection/transport abilities. Further, the compound may be used as the material of the light emitting layer of the organic EL device to provide improved efficiency and lifetime.

In the present invention, the light emitting layer may include a phosphorescent guest material or a fluorescent guest material. Preferably, the compounds represented by Chemical Formulas 1 to 4 may be included as the blue, green and/or red phosphorescent host, fluorescent host, hole transport material and/or hole transferring material in the organic electroluminescent device.

Further, the compounds represented by Chemical Formulas 1 to 4 according to the present invention have the glass transition temperature of 150° C. or more. Therefore, in the case where the compound is used as the organic layer of the organic electroluminescent device, since occurrence of crystallization in the organic electroluminescent device is minimized, a driving voltage of the device may be reduced, and light emitting efficiency, luminance, thermal stability, and lifetime properties may be improved.

A non-limiting example of the organic EL device structure according to the present invention may be a matter where a substrate, an anode, a hole injection layer, a hole transport layer, a light emitting layer, an electron transport layer, and a cathode are sequentially laminated. In this case, one or more of the light emitting layer, the hole injection layer, and the hole transport layer may include the compounds represented by Chemical Formulas 1 to 4. The electron injection layer may be positioned on the electron transport layer.

Further, the organic electroluminescent device according to the present invention, as described above, may have the structure where the anode, one or more organic layers, and the cathode are sequentially laminated, and an insulating layer or an adhesion layer may be interposed at an interface between the electrode and the organic layer.

In the organic electroluminescent device of the present invention, the organic layer comprising the compounds of Chemical Formulas 1 to 4 may be formed by a vacuum deposition method or a solution coating method. Examples of the solution coating include spin coating, dip coating, doctor blading, inkjet printing, a heat transferring method, and the like, but are not limited thereto.

The organic electroluminescent device of the present invention may be manufactured by forming the organic layer and the electrode by using a material and a method known in the art, except that one or more organic layers in the device include the compounds represented by Chemical Formulas 1 to 4 of the present invention.

For example, a silicon wafer, quartz, a glass plate, a metal plate, a plastic film, a sheet, or the like may be used as the substrate.

Examples of the anode material include metal such as vanadium, chrome, copper, zinc, and gold or an alloy thereof; metal oxides such as zinc oxides, indium oxides, indium tin oxides (ITO), and indium zinc oxides (IZO); a combination of metal and oxides such as ZnO:Al or $SnO_2$:Sb; conductive polymers such as polythiophene, poly(3-methylthiophene), poly[3,4-(ethylene-1,2-dioxy)thiophene] (PEDT), polypyrrole, and polyaniline; carbon blacks, and the like, but are not limited thereto.

Examples of the cathode material include metal such as magnesium, calcium, sodium, potassium, titanium, indium, yttrium, lithium, gadolinium, aluminum, silver, tin, or lead or an alloy thereof; a multilayered structure material such as LiF/Al or $LiO_2$/Al and the like, but are not limited thereto.

The hole injection layer, the hole transport layer, the electron transport layer, and the electron injection layer are not particularly limited, and a general material known in the art may be used.

MODE FOR THE INVENTION

Hereinafter, the present invention will be described in detail through the Examples. However, the following Examples are set forth to illustrate but are not to be construed to limit the present invention.

Synthetic Example 1

Synthesis of 2-bromo-9H-carbazole

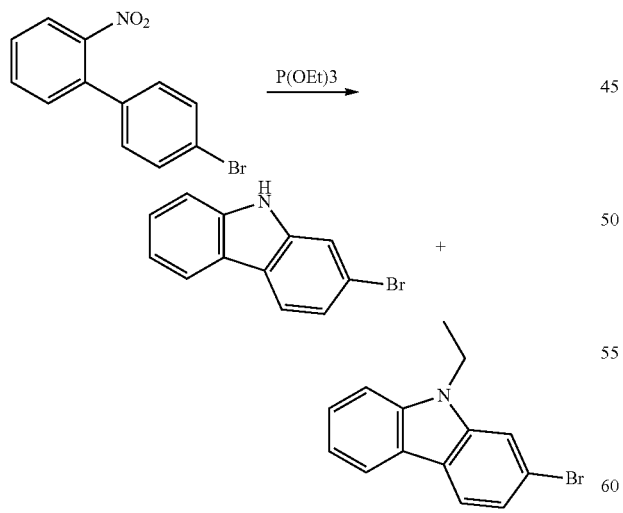

17.93 g (64.47 mmol) of 4'-bromo-2-nitrobiphenyl and 56.09 mL (322.37 mmol) of triethyl phosphate were put into a round bottom flask under nitrogen, and then refluxed and agitated for 5 hours. After the reaction was finished, the solvent was removed by distillation, and the column was used at a ratio of hexane:MC=3:2 (v/v) to obtain 7.2 g of 2-bromo-9H-carbazole and 4.26 g of 2-bromo-9-ethyl-9H-carbazole.

2-bromo-9H-carbazole $^1$H NMR: 7.13 (t, 1H), 7.25 (dd, 1H), 7.34 (t, 1H), 7.40 (d, 1H), 7.57 (d, 1H), 7.94 (d, 1H), 8.02 (d, 1H), 10.42 (s, 1H).

GC-Mass (theoretical value: 244.98 g/mol, measured value: 245 g/mol).

2-bromo-9-ethylcarbazole $^1$H NMR: 1.35 (t, 3H), 4.37 (dd, 2H), 7.17 (t, 1H), 7.28 (dd, 1H), 7.42 (m, 2H), 7.70 (d, 1H), 7.95 (d, 1H), 8.04 (d, 1H).

GC-Mass (theoretical value: 273.02 g/mol, measured value: 273 g/mol).

Synthetic Example 2

Synthesis of 2-bromo-9-phenylcarbazole

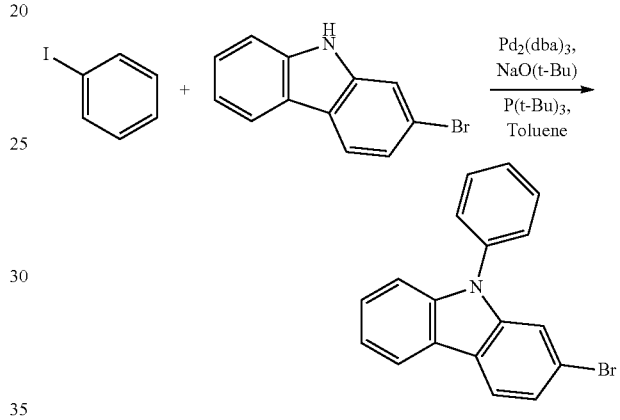

30.51 g (149.56 mmol) of iodobenzene, 18.32 g (74.78 mmol) of 2-bromo-9H-carbazole, 14.37 g (149.56 mmol) of sodium t-butoxide, and 1.81 ml (7.48 mmol) of tritertbutylphosphine were dissolved in 300 ml of toluene, and 0.68 g (0.75 mmol) of $Pd_2(dba)_3$ was added thereto, and refluxed and agitated for 12 hours. After the reaction was finished, extraction was performed by dichloromethane, filtering was performed by silica gel, and the column was used at a ratio of hexane:MC=9:1 (v/v) to obtain 8.99 g of 2-bromo-9-phenylcarbazole (yield 37%).

$^1$H NMR: 7.24 (t, 1H), 7.36 (m, 3H), 7.50 (dd, 2H), 7.58 (t, 2H), 7.65 (t, 2H), 8.06 (d, 1H), 8.13 (d, 1H).

GC-Mass (theoretical value: 321.02 g/mol, measured value: 321 g/mol).

Synthetic Example 3

Synthesis of 9-ethyl-2-(4,4,5,5-tetramethyl-1,3,2-dioxaborolan-2-yl)carbazole

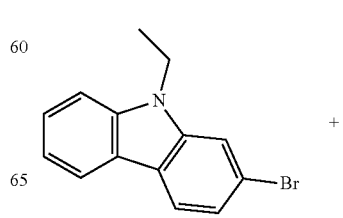

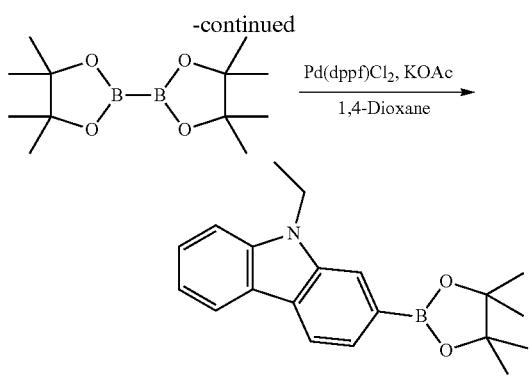

4.26 g (15.60 mmol) of 2-bromo-9-ethylcarbazole, 5.15 g (20.28 mmol) of 4,4,4',4',5,5,5',5'-octamethyl-2,2'-bi(1,3,2-dioxaborolane), 3.06 g (31.21 mmol) of potassium acetate, and 0.25 g (0.31 mmol) of Pd(dppf)Cl$_2$ were dissolved in 50 ml of 1,4-dioxane, and then refluxed and agitated for 12 hours. After the reaction was finished, extraction was performed by dichloromethane, filtering was performed by silica gel, and the column was used at a ratio of hexane:MC=7:3 (v/v) to obtain 4.8 g of 9-ethyl-2-(4,4,5,5-tetramethyl-1,3,2-dioxaborolan-2-yl)carbazole (yield 96%).

$^1$H NMR: 1.36 (s, 12H), 1.39 (t, 3H), 4.45 (dd, 2H), 7.14 (t, 1H), 7.41 (t, 1H), 7.47 (d, 1H), 7.60 (d, 1H), 7.90 (s, 1H), 8.07 (dd, 2H).

GC-Mass (theoretical value: 321.19 g/mol, measured value: 321 g/mol).

Synthetic Example 4

Synthesis of 9-phenyl-2-(4,4,5,5-tetramethyl-1,3,2-dioxaborolan-2-yl)carbazole

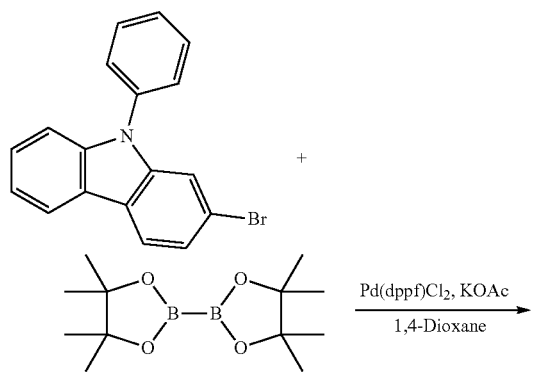

8.3 g (25.86 mmol) of 2-bromo-9-phenylcarbazole, 8.54 g (33.61 mmol) of 4,4,4',4',5,5,5',5'-octamethyl-2,2'-bi(1,3,2-dioxaborolane), 5.08 g (51.71 mmol) of potassium acetate, and 0.42 g (0.52 mmol) of Pd(dppf)Cl$_2$ were dissolved in 100 ml of 1,4-dioxane, and then refluxed and agitated for 12 hours. After the reaction was finished, extraction was performed by dichloromethane, filtering was performed by silica gel, and the column was used at a ratio of hexane:MC=7:3 (v/v) to obtain 9.2 g of 9-phenyl-2-(4,4,5,5-tetramethyl-1,3,2-dioxaborolan-2-yl)carbazole (yield 94%).

$^1$H NMR: 1.31 (s, 12H), 7.23 (t, 1H), 7.36 (m, 2H), 7.49 (t, 1H), 7.58 (dd, 2H), 7.64 (t, 2H), 7.67 (d, 1H), 7.79 (s, 1H), 8.14 (dd, 2H).

GC-Mass (theoretical value: 369.19 g/mol, measured value: 369 g/mol).

Synthetic Example 5

Synthesis of 2-bromo-5'-methoxybiphenyl

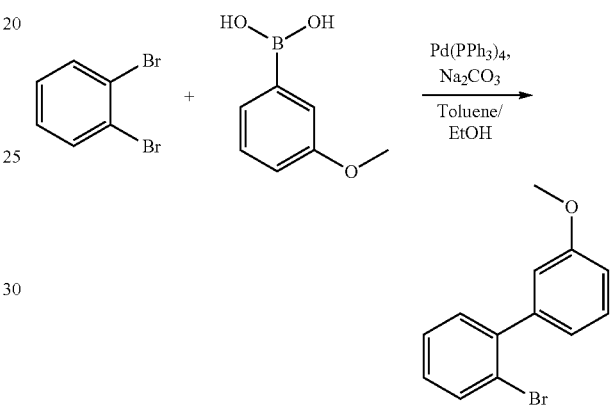

20.0 g (85.52 mmol) of 1,2-dibromobenzene, 11.70 g (76.97 mmol) of 3-methoxyphenylboronic acid, 0.99 g (0.86 mmol) of Pd(PPh$_3$)$_4$, and 18.13 g (171.04 mmol) of sodium carbonate were put, suspended in 300 ml of toluene and 100 ml of ethanol, and refluxed and agitated for 12 hours. After the reaction was finished, extraction was performed by dichloromethane, filtering was performed by silica gel, and the column was used at a ratio of hexane:MC=4:1 (v/v) to obtain 14.12 g of 2-bromo-3'-methoxybiphenyl that was the target compound (yield 63%).

$^1$H NMR: 3.47 (s, 3H), 6.73 (t, 1H), 7.13 (t, 1H), 7.35 (t, 1H), 7.40 (m, 4H), 7.54 (d, 1H).

GC-Mass (theoretical value: 262.00 g/mol, measured value: 262 g/mol).

Synthetic Example 6

Synthesis of 9-ethyl-2-(3'-methoxybiphenyl-2-yl)carbazole

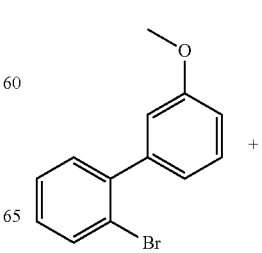

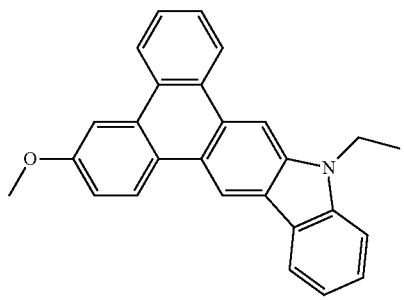

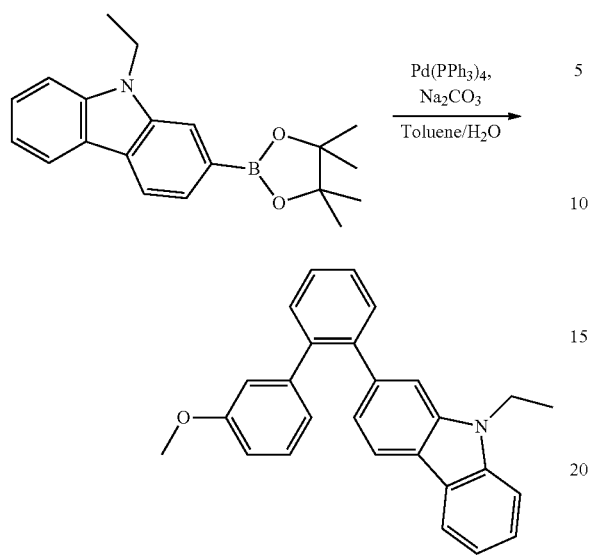

3.93 g (15.00 mmol) of 2-bromo-3'-methoxybiphenyl, 5.3 g (16.50 mmol) of 9-ethyl-2-(4,4,5,5-tetramethyl-1,3,2-dioxaborolan-2-yl)carbazole, and 0.35 g (0.30 mmol) of Pd(PPh$_3$)$_4$ were dissolved in 50 ml of toluene, and 4.77 g (45.00 mmol) of Na$_2$CO$_3$ was put into 25 ml of distilled water and then refluxed and agitated for 5 hours. After the reaction was finished, extraction was performed by dichloromethane, filtering was performed by silica gel, and the column was used at a ratio of hexane:MC=7:3 (v/v) to obtain 3.90 g of 9-ethyl-2-(3'-methoxybiphenyl-2-yl)carbazole (yield 69%).

$^1$H NMR: 1.17 (t, 3H), 3.48 (s, 3H), 4.23 (dd, 2H), 6.65 (dd, 1H), 6.67 (dd, 2H), 7.03 (m, 2H), 7.11 (t, 1H), 7.21 (s, 1H), 7.36 (t, 1H), 7.41 (m, 4H), 7.54 (dd, 1H), 7.93 (d, 1H), 8.00 (d, 1H).

GC-Mass (theoretical value: 377.18 g/mol, measured value: 377 g/mol).

Synthetic Example 7

Synthesis of
10-ethyl-3-methoxy-10H-phenanthro[9,10-b]carbazole

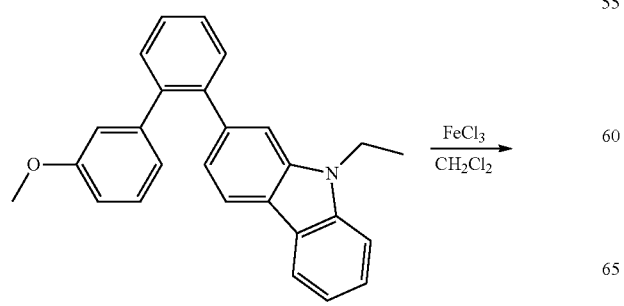

3.90 g (10.34 mmol) of 9-ethyl-2-(3'-methoxybiphenyl-2-yl)carbazole was dissolved in 50 ml of dichloromethane 50 ml, and 3.52 g (21.71 mmol) of FeCl$_3$ was slowly put thereinto at normal temperature and agitated for 12 hours. After agitation, 3.52 g (21.71 mmol) of FeCl$_3$ was further put thereinto and agitated for 1 hour. After the reaction was finished, quenching was performed by distilled water and ethanol, the organic layer was separated, filtering was performed by silica gel, and the column was used at a ratio of hexane:MC=7:3 (v/v) to obtain 2.5 g of 10-ethyl-3-methoxy-10H-phenanthro [9,10-b]carbazole (yield 64%).

$^1$H NMR: 1.51 (t, 3H), 4.00 (s, 3H), 4.61 (dd, 2H), 7.23 (t, 1H), 7.28 (dd, 1H), 7.48 (m, 2H), 7.61 (m, 2H), 8.12 (d, 1H), 8.32 (d, 1H), 8.67 (dd, 1H), 8.69 (s, 1H), 8.81 (d, 1H), 8.88 (d, 1H), 9.38 (s, 1H).

GC-Mass (theoretical value: 375.16 g/mol, measured value: 375 g/mol).

Synthetic Example 8

Synthesis of
10-ethyl-10H-phenanthro[9,10-b]carbazol-3-ol

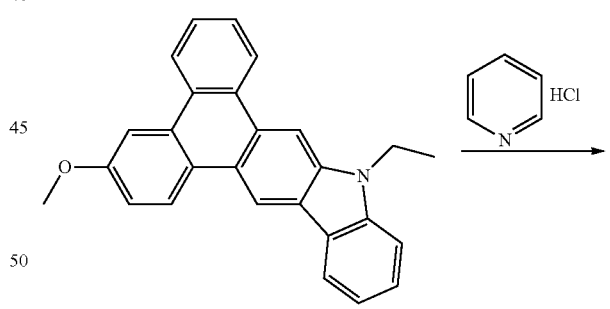

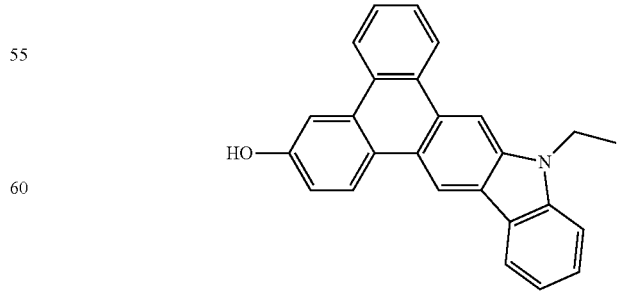

2.5 g (6.66 mmol) of 10-ethyl-3-methoxy-10H-phenanthro [9,10-b)]carbazole and 3.85 g (33.32 mmol) of pyridine hydrochloride were put into a reaction vessel, and refluxed and agitated at 220° C. for 2 hours. After the reaction was finished, distilled water was slowly added, the generated solid was filtered, and the column was used at a ratio of hexane: EA=4:1 (v/v) to obtain 2.2 g of 10-ethyl-10H-phenanthro[9, 10-b]carbazol-3-ol that was the target compound (yield 91%).

$^1$H NMR: 1.50 (t, 3H), 4.60 (dd, 2H), 7.15 (dd, 1H), 7.21 (t, 1H), 7.48 (m, 2H), 7.58 (m, 2H), 7.99 (d, 1H), 8.30 (d, 1H), 8.46 (s, 1H), 8.55 (t, 1He), 8.68 (s, 1H), 8.74 (d, 1H), 8.86 (d, 1H), 9.34 (s, 1H).

GC-Mass (theoretical value: 361.15 g/mol, measured value: 361 g/mol).

Synthetic Example 9

Synthesis of 10-ethyl-10H-phenanthro[9,10-b]carbazol-3-yl trifluoromethansulfonate 2.2 g (6.09 mmol) of 10-ethyl-10H-phenanthro[9,10-b] carbazol-3-ol and 35 ml of pyridine were put into the reaction vessel and agitated. 1.23 ml (7.31 mmol) of trifluoromethanesulfonyl anhydride was slowly put into the reactant and agitated for 12 hours. After the reaction was finished, pyridine was removed, washing was performed three times by methanol, hexane/MC recrystallization was performed to obtain 2.69 g of 10-ethyl-10H-phenanthro[9,10-b]carbazol-3-yl trifluoromethanesulfonate that was the target compound (yield 90%).

$^1$H NMR: 1.47 (t, 3H), 4.62 (dd, 2H), 7.17 (dd, 1H), 7.20 (t, 1H), 7.45 (m, 2H), 7.56 (m, 2H), 7.95 (d, 1H), 8.25 (d, 1H), 8.42 (s, 1H), 8.58 (t, 1H), 8.71 (d, 1H), 8.88 (d, 1H), 9.32 (s, 1H).

GC-Mass (theoretical value: 493.10 g/mol, measured value: 493 g/mol).

Example 1

Synthesis of Inv-35

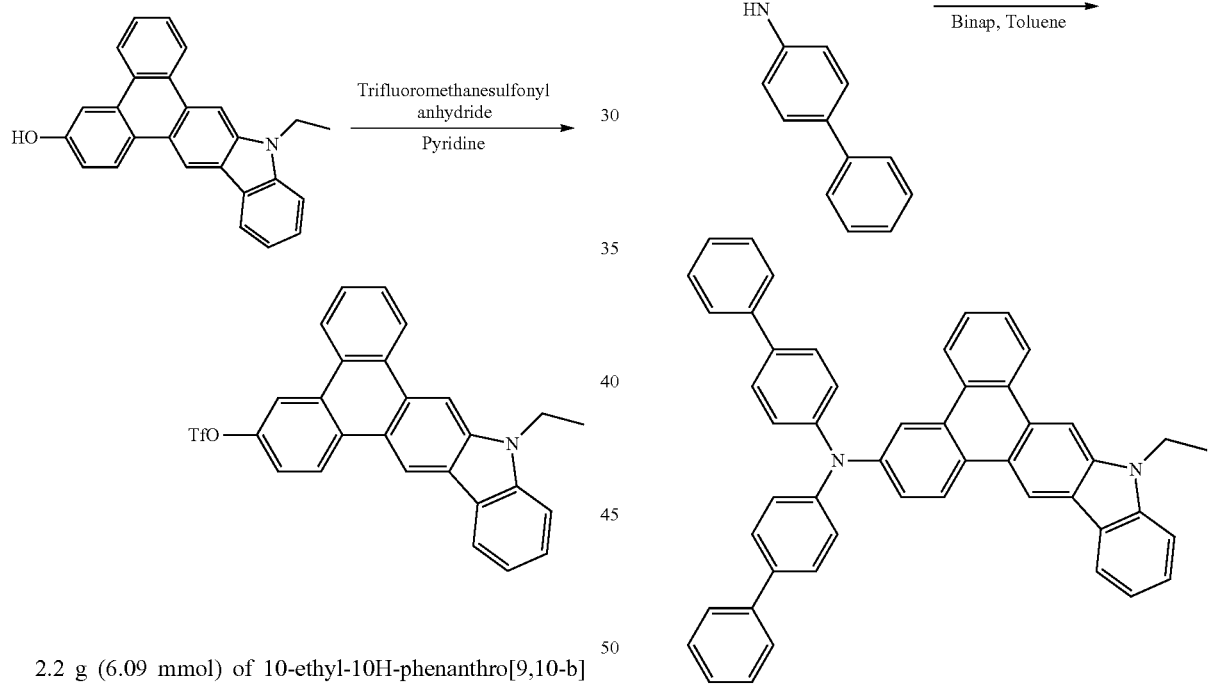

2.69 g (5.46 mmol) of 10-ethyl-10H-phenanthro[9,10-b] carbazol-3-yl trifluoromethanesulfonate synthesized in Synthetic Example 9, 2.63 g (8.18 mmol) of dibiphenyl-4-ylamine, 0.04 g (0.16 mmol) of Pd(OAc)$_2$, 0.20 g (0.33 mmol) of Binap, and 1.51 g (10.91 mmol) of K$_2$CO$_3$ were put, suspended in 30 ml of toluene, and refluxed and agitated for 12 hours. After the reaction was finished, extraction was performed by dichloromethane, filtering was performed by silica gel, and the column was used at a ratio of hexane: MC=4:1 (v/v) to obtain 2.83 g of N,N-di(biphenyl-4-yl)-10-ethyl-10H-phenanthro[9,10-b]carbazol-3-amine that was the target compound (yield 78%).

$^1$H NMR: 1.48 (t, 3H), 4.61 (dd, 2H), 6.57 (dd, 4H), 7.16 (dd, 1H), 7.19 (t, 1H), 7.46 (m, 12H), 7.55 (m, 2H), 7.78 (dd,

4H), 7.93 (d, 1H), 8.21 (d, 1H), 8.44 (s, 1H), 8.56 (t, 1H), 8.73 (d, 1H), 8.85 (d, 1H), 9.17 (s, 1H).

GC-Mass (theoretical value: 664.29 g/mol, measured value: 664 g/mol).

Example 2

Synthesis of Inv-1

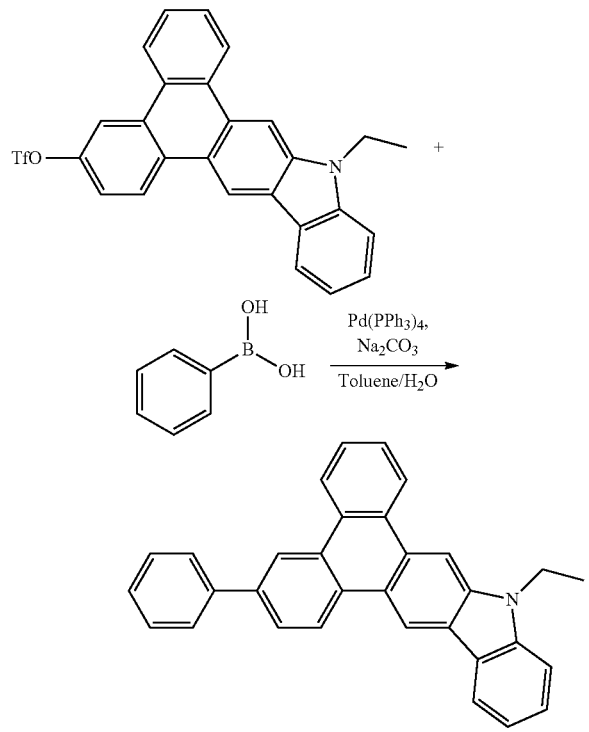

10.0 g (20.28 mmol) of 10-ethyl-10H-phenanthro[9,10-b]carbazol-3-yl trifluoromethanesulfonate synthesized in Synthetic Example 9, 3.71 g (30.42 mmol) of phenylboronic acid, and 0.23 g (0.20 mmol) of Pd(PPh₃)₄ were dissolved in 150 ml of toluene, and 4.30 g (40.56 mmol) of Na₂CO₃ was put into 50 ml of distilled water, and then refluxed and agitated for 5 hours. After the reaction was finished, extraction was performed by dichloromethane, filtering was performed by silica gel, and the column was used at a ratio of Hexane:MC=7:3 (v/v) to obtain 5.81 g of 10-ethyl-3-phenyl-10H-phenanthro[9,10-b]carbazole (yield 68%).

¹H NMR: 1.45 (t, 3H), 4.63 (dd, 2H), 7.16 (dd, 1H), 7.22 (t, 1H), 7.45 (m, 5H), 7.55 (m, 2H), 7.79 (dd, 2H), 7.98 (d, 1H), 8.21 (d, 1H), 8.41 (s, 1H), 8.59 (t, 1H), 8.68 (d, 1H), 8.89 (d, 1H), 9.31 (s, 1H).

GC-Mass (theoretical value: 421.18 g/mol, measured value: 421 g/mol).

Example 3

Synthesis of Inv-6

Synthesis was performed by the same method as Example 2 to obtain 6.96 g of Inv-6 that was the target compound (yield 69%), except that 6.03 g (30.42 mmol) of biphenyl-3-ylboronic acid was put thereinto.

¹H NMR: 1.46 (t, 3H), 4.64 (dd, 2H), 7.18 (dd, 1H), 7.23 (t, 1H), 7.46 (m, 8H), 7.56 (m, 2H), 7.80 (dd, 3H), 7.99 (d, 1H), 8.22 (d, 1H), 8.43 (s, 1H), 8.61 (t, 1H), 8.67 (d, 1H), 8.88 (d, 1H), 9.33 (s, 1H).

GC-Mass (theoretical value: 497.21 g/mol, measured value: 497 g/mol).

Example 4

Synthesis of Inv-12

Synthesis was performed by the same method as Example 2 to obtain 8.32 g of Inv-12 that was the target compound (yield 70%), except that 11.23 g (30.42 mmol) of 9-phenyl-3-(4,4,5,5-tetramethyl-1,3,2-dioxaborolan-2-yl)carbazole was put thereinto.

¹H NMR: 1.46 (t, 3H), 4.63 (dd, 2H), 7.16 (dd, 1H), 7.21 (m, 3H), 7.46 (m, 10H), 7.61 (m, 3H), 7.96 (d, 1H), 8.23 (m, 2H), 8.43 (s, 11-1), 8.59 (t, 1H), 8.70 (d, 1H), 8.90 (d, 1H), 9.28 (s, 1H).

GC-Mass (theoretical value: 586.24 g/mol, measured value: 586 g/mol).

Example 5

Synthesis of Inv-17

Synthesis was performed by the same method as Example 2 to obtain 8.32 g of Inv-12 that was the target compound (yield 70%), except that 11.23 g (30.42 mmol) of N,N-diphenyl-3-(4,4,5,5-tetramethyl-1,3,2-dioxaborolan-2-yl)aniline was put thereinto.

¹H NMR: 1.46 (t, 3H), 4.62 (dd, 2H), 6.51 (m, 5H), 6.65 (d, 1H), 6.89 (t, 1H), 7.03 (m, 7H), 7.16 (dd, 1H), 7.20 (t, 1H), 7.42 (m, 2H), 7.58 (m, 2H), 7.98 (d, 1H), 8.21 (d, 1H), 8.40 (s, 1H), 8.59 (t, 1H), 8.73 (d, 1H), 8.92 (d, 1H), 9.29 (s, 1H).

GC-Mass (theoretical value: 588.26 g/mol, measured value: 588 g/mol).

Example 6

Synthesis of Inv-23

Synthesis was performed by the same method as Example 2 to obtain 7.79 g of Inv-23 that was the target compound (yield 59%), except that 13.21 g (30.42 mmol) of 2,4-diphenyl-6-(3-(4,4,5,5-tetramethyl-1,3,2-dioxaborolan-2-yl)phenyl)pyrimidine was put thereinto.

¹H NMR: 1.46 (t, 3H), 4.61 (dd, 2H), 7.18 (dd, 1H), 7.21 (t, 1H), 7.44 (m, 11H), 7.55 (m, 2H), 7.71 (m, 3H), 7.96 (d, 1H), 8.26 (m, 4H), 8.43 (s, 1H), 8.57 (t, 1H), 8.73 (d, 1H), 8.89 (d, 1H), 9.34 (s, 1H).

GC-Mass (theoretical value: 651.27 g/mol, measured value: 651 g/mol).

Example 7

Synthesis of Inv-46

Synthesis was performed by the same method as Example 2 to obtain 6.65 g of Inv-46 that was the target compound (yield 66%), except that 10.0 g (18.48 mmol) of 10-phenyl-10H-phenanthro[9,10-b]carbazol-3-yl trifluoromethanesulfonate obtained by synthesizing the material synthesized in Synthetic Example 4 by using the same method as Synthetic Examples 6 to 9 and 6.03 g (27.72 mmol) of biphenyl-3-ylboronic acid were put thereinto.

¹H NMR 7.15 (dd, 1H), 7.26 (m, 3H), 7.45 (m, 8H), 7.55 (m, 5H), 7.79 (dd, 3H), 7.97 (d, 1H), 8.21 (d, 1H), 8.45 (s, 1H), 8.60 (t, 1H), 8.69 (d, 1H), 8.89 (d, 1H), 9.31 (s, 1H).

GC-Mass (theoretical value: 545.21 g/mol, measured value: 545 g/mol).

Example 8

Synthesis of Inv-52

Synthesis was performed by the same method as Example 2 to obtain 8.20 g of Inv-52 that was the target compound (yield 70%), except that 10.0 g (18.48 mmol) of 10-phenyl-10H-phenanthro[9,10-b]carbazol-3-yl trifluoromethanesulfonate obtained by synthesizing the material synthesized in Synthetic Example 4 by using the same method as Synthetic Examples 6 to 9 and 10.23 g (27.72 mmol) of 9-phenyl-3-(4,4,5,5-tetramethyl-1,3,2-dioxaborolan-2-yl)carbazole were put thereinto.

¹H NMR: 7.17 (dd, 1H), 7.26 (m, 5H), 7.46 (m, 10H), 7.60 (m, 6H), 7.95 (d, 1H), 8.22 (m, 2H), 8.42 (s, 1H), 8.61 (t, 1H), 8.75 (d, 1H), 8.91 (d, 1H), 9.29 (s, 1H).

GC-Mass (theoretical value: 634.24 g/mol, measured value: 634 g/mol).

Example 9

Synthesis of Inv-63

Synthesis was performed by the same method as Example 2 to obtain 8.40 g of Inv-63 that was the target compound (yield 65%), except that 10.0 g (18.48 mmol) of 10-phenyl-10H-phenanthro[9,10-b]carbazol-3-yl trifluoromethanesulfonate obtained by synthesizing the material synthesized in Synthetic Example 4 by using the same method as Synthetic Examples 6 to 9 and 12.04 g (27.72 mmol) of 2,4-diphenyl-6-(3-(4,4,5,5-tetramethyl-1,3,2-dioxaborolan-2-yl)phenyl)pyrimidine were put thereinto.

¹H NMR: 7.17 (dd, 1H), 7.26 (m, 3H), 7.42 (m, 11H), 7.55 (m, 5H), 7.76 (m, 3H), 7.98 (d, 1H), 8.21 (m, 4H), 8.44 (s, 1H), 8.59 (t, 1H), 8.74 (d, 1H), 8.90 (d, 1H), 9.26 (s, 1H).

GC-Mass (theoretical value: 699.27 g/mol, measured value: 699 g/mol).

Example 10

Synthesis of Inv-72

Synthesis was performed by the same method as Example 1 to obtain 8.66 g of Inv-72 that was the target compound (yield 71%), except that 10.0 g (18.48 mmol) of 10-phenyl-10H-phenanthro[9,10-b]carbazol-3-yl trifluoromethanesulfonate obtained by synthesizing the material synthesized in Synthetic Example 4 by using the same method as Synthetic Examples 6 to 9 and 7.46 g (27.72 mmol) of dinaphthalen-1-ylamine were put thereinto.

¹H NMR: 6.61 (d, 2H), 7.17 (dd, 1H), 7.25 (m, 7H), 7.44 (m, 6H), 7.57 (m, 7H), 7.96 (d, 1H), 8.21 (m, 3H), 8.44 (s, 1H), 8.56 (t, 1H), 8.69 (d, 1H), 8.85 (d, 1H), 9.35 (s, 1H).

GC-Mass (theoretical value: 660.26 g/mol, measured value: 660 g/mol).

Example 11

Synthesis of Inv-75

Synthesis was performed by the same method as Example 1 to obtain 9.21 g of Inv-75 that was the target compound (yield 70%), except that 10.0 g (18.48 mmol) of 10-phenyl-10H-phenanthro[9,10-b]carbazol-3-yl trifluoromethanesulfonate obtained by synthesizing the material synthesized in Synthetic Example 4 by using the same method as Synthetic Examples 6 to 9 and 8.76 g (27.72 mmol) of dibiphenyl-4-ylamine were put thereinto.

¹H NMR: 6.59 (dd, 4H), 7.17 (dd, 1H), 7.26 (m, 3H), 7.45 (m, 12H), 7.55 (m, 5H), 7.77 (dd, 4H), 7.94 (d, 1H), 8.23 (d, 1H), 8.42 (s, 1H), 8.57 (t, 1H), 8.71 (d, 1H), 8.86 (d, 1H), 9.19 (s, 1H).

GC-Mass (theoretical value: 712.29 g/mol, measured value: 712 g/mol).

Example 12

Synthesis of Inv-80

Synthesis was performed by the same method as Example 1 to obtain 14.18 g of Inv-80 that was the target compound (yield 68%), except that 10.0 g (18.48 mmol) of 10-phenyl-10H-phenanthro[9,10-b]carbazol-3-yl trifluoromethanesulfonate obtained by synthesizing the material synthesized in Synthetic Example 4 by using the same method as Synthetic Examples 6 to 9 and 10.01 g (27.72 mmol) of N-(biphenyl-4-yl)-9,9-dimethyl-9H-fluoren-2-amine were put thereinto.

¹H NMR: 1.58 (s, 6H), 6.53 (dd, 4H), 7.16 (dd, 1H), 7.25 (m, 3H), 7.44 (m, 10H), 7.54 (m, 5H), 7.78 (m, 4H), 7.95 (d, 1H), 8.21 (d, 1H), 8.43 (s, 1H), 8.55 (t, 1H), 8.72 (d, 1H), 8.89 (d, 1H), 9.17 (s, 1H).

GC-Mass (theoretical value: 752.32 g/mol, measured value: 752 g/mol).

Examples 13 to 17

Manufacturing and Evaluation of the Organic EL Device

The glass substrate on which ITO (Indium tin oxide) was applied in a thin film in a thickness of 1500 Å was subjected to ultrasonic wave washing by distilled water. After the washing by distilled water was finished, the substrate was subjected to the ultrasonic wave washing by the solvent such as isopropyl alcohol, acetone, and methanol, dried, transported to the plasma washing machine, washed by using the oxygen plasma for 5 min, and transported to the vacuum deposition machine.

After NPB (40 nm)/Inv+10% Ir(ppy)$_3$ (20 nm)/BCP (10 nm)/Alq$_3$ (40 nm)/LiF (1 nm)/Al were sequentially constituted on the ITO transparent electrode prepared as described above to form the light emitting device, light emitting properties thereof were evaluated, and the results thereof are described in the following Table 1. Herein, the compounds applied to Inv are described in the following Table 1.

Examples 18 to 24

Manufacturing and Evaluation of the Organic EL Device

The glass substrate on which ITO (Indium tin oxide) was applied in a thin film in a thickness of 1500 Å was subjected to ultrasonic wave washing by distilled water. After the washing by distilled water was finished, the substrate was subjected to the ultrasonic wave washing by the solvent such as isopropyl alcohol, acetone, and methanol, dried, transported to the plasma washing machine, washed by using the oxygen plasma for 5 min, and transported to the vacuum deposition machine.

After Inv (40 nm)/CBP+10% Ir(ppy)$_3$ (20 nm)/BCP (10 nm)/Alq$_3$ (40 nm)/LiF (1 nm)/Al were sequentially constituted on the ITO transparent electrode prepared as described above to form the light emitting device, light emitting properties thereof were evaluated, and the results thereof are described in the following Table 2. Herein, the compounds applied to Inv are described in the following Table 2.

Comparative Example 1

After NPB (40 nm)/CBP+10% Ir(ppy)$_3$ (20 nm)/BCP (10 nm)/Alq$_3$ (40 nm)/LiF (1 nm)/Al were sequentially constituted on the electrode prepared in Examples 13 to 24 to form the light emitting device, light emitting properties thereof were evaluated by the same method as Example 1.

For reference, the structures of NPB, CBP, Ir(ppy)$_3$, and BCP are as follows.

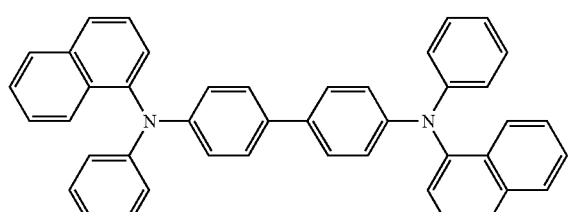

NPB

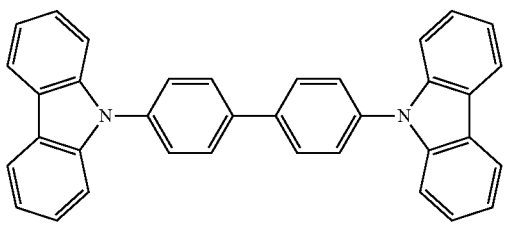

CBP

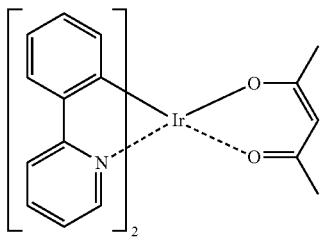

Ir(ppy)2(acac)

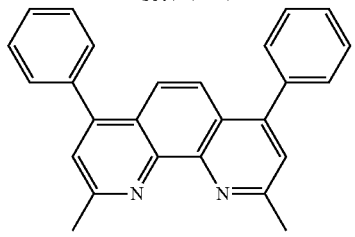

BCP

TABLE 1

| | Voltage (V) | Luminance (cd/m2) | Color | Efficiency (cd/A) |
|---|---|---|---|---|
| Inv-1 (Example 13) | 6.43 | 212 | Green | 21.2 |
| Inv-6 (Example 14) | 6.03 | 265 | Green | 26.5 |
| Inv-23 (Example 15) | 5.65 | 325 | Green | 32.5 |
| Inv-46 (Example 16) | 6.01 | 273 | Green | 27.3 |
| Inv-63 (Example 17) | 5.54 | 336 | Green | 33.6 |
| Comparative Example 1 | 7.94 | 174 | Green | 17.4 |

TABLE 2

| | Voltage (V) | Luminance (cd/m2) | Color | Efficiency (cd/A) |
|---|---|---|---|---|
| Inv-12 (Example 18) | 6.13 | 185 | Green | 18.5 |
| Inv-17 (Example 19) | 6.35 | 179 | Green | 17.9 |
| Inv-35 (Example 20) | 5.86 | 204 | Green | 20.4 |
| Inv-52 (Example 21) | 6.02 | 187 | Green | 18.7 |
| Inv-72 (Example 22) | 5.98 | 199 | Green | 19.9 |
| Inv-75 (Example 23) | 5.64 | 235 | Green | 23.5 |
| Inv-80 (Example 24) | 5.71 | 213 | Green | 21.3 |
| Comparative Example 1 | 7.94 | 174 | Green | 17.4 |

From the test results, it could be confirmed that the organic light emitting device of Examples 13 to 24 adopting the phenanthrocarbazole-based compound according to the present invention exhibited largely better performance in terms of voltage and efficiency as compared to the known organic light emitting device of Comparative Example 1 adopting CBP (see Tables 1 to 2).

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

The invention claimed is:

1. A material for an organic electroluminescent device represented by the following Chemical Formula 1:

[Chemical Formula 1]

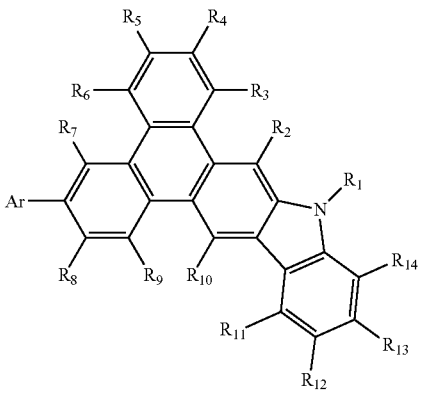

wherein,

Ar is an aromatic hydrocarbon ring group or an aromatic amine ring group, and selected from the group consisting of benzene, naphthalene, biphenyl, anthracene, phenanthrene, pyrene, perylene, triphenylene, and triphenyl amine, $R_1$ to $R_{14}$ are each independently selected from the group consisting of hydrogen, deuterium, a halogen atom, an alkyl group having 1 to 40 carbon atoms, a hetero-ring group having 3 to 40 nucleus atoms, an alkoxy group having 1 to 40 carbon atoms, an aromatic hydrocarbon group having 6 to 40 nucleus carbon atoms, an aryloxy group having 6 to 40 carbon atoms, an arylalkyl group having 7 to 40 carbon atoms, an alkenyl group having 2 to 40 carbon atoms, an alkylamino group having 1 to 40 carbon atoms, an arylamino group having 6 to 40 carbon atoms, an arylalkylamino group having 7 to 40 carbon atoms, an alkylsilyl group having 3 to 20 carbon atoms, an arylsilyl group having 8 to 40 carbon atoms, a ketoaryl group having 7 to 40 carbon atoms, a halogenated alkyl group having 1 to 40 carbon atoms, and a cyano group, $R_1$ to $R_{14}$ may each independently bind with adjacent substituents, or the substituents introduced to Ar may each independently bind with adjacent substituents to form a saturated or unsaturated ring structure.

2. A material for an organic electroluminescent device represented by the following Chemical Formula 2:

[Chemical Formula 2]

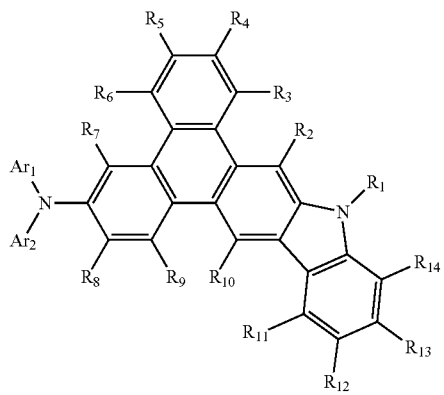

wherein, $Ar_1$ and $Ar_2$ may be the same as or different from each other, and are each independently selected from the group consisting of benzene, naphthalene, biphenyl, anthracene, phenanthrene, pyrene, perylene, and triphenylene, and in $Ar_1$ and $Ar_2$, the adjacent substituents may be bonded to each other to form a saturated or unsaturated ring structure, $R_1$ to $R_{14}$ are each independently selected from the group consisting of hydrogen, deuterium, a halogen atom, an alkyl group having 1 to 40 carbon atoms, a hetero-ring group having 3 to 40 nucleus atoms, an alkoxy group having 1 to 40 carbon atoms, an aromatic hydrocarbon group having 6 to 40 nucleus carbon atoms, an aryloxy group having 6 to 40 carbon atoms, an arylalkyl group having 7 to 40 carbon atoms, an alkenyl group having 2 to 40 carbon atoms, an alkylamino group having 1 to 40 carbon atoms, an arylamino group having 6 to 40 carbon atoms, an arylalkylamino group having 7 to 40 carbon atoms, an alkylsilyl group having 3 to 20 carbon atoms, an arylsilyl group having 8 to 40 carbon atoms, a ketoaryl group having 7 to 40 carbon atoms, a halogenated alkyl group having 1 to 40 carbon atoms, and a cyano group, and $R_1$ to $R_4$, $R_5$ to $R_8$, $R_9$ to $R_{12}$, and $R_{13}$ to $R_{14}$ may each independently bind with adjacent substituents, or $R_{12}$ and $R_{13}$ may be bonded to each other to form a saturated or unsaturated ring structure.

3. A material for an organic electroluminescent device represented by the following Chemical Formula 3:

[Chemical Formula 3]

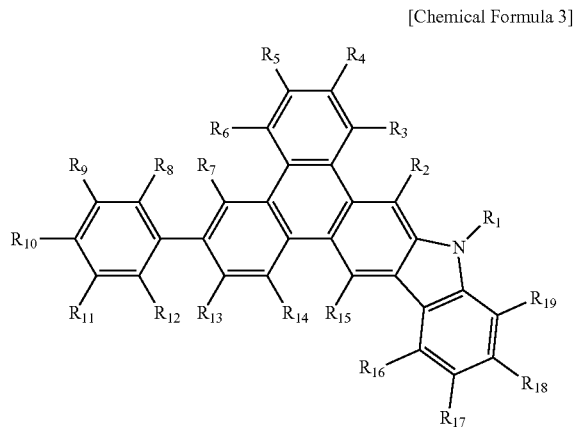

wherein, $R_1$ to R19 are each independently selected from the group consisting of hydrogen, deuterium, a halogen atom, an alkyl group having 1 to 40 carbon atoms, a hetero-ring group having 3 to 40 nucleus atoms, an alkoxy group having 1 to 40 carbon atoms, an aromatic hydrocarbon group having 6 to 40 nucleus carbon atoms, an aryloxy group having 6 to 40 carbon atoms, an arylalkyl group having 7 to 40 carbon atoms, an alkenyl group having 2 to 40 carbon atoms, an alkylamino group having 1 to 40 carbon atoms, an arylamino group having 6 to 40 carbon atoms, an arylalkylamino group having 7 to 40 carbon atoms, an alkylsilyl group having 3 to 20 carbon atoms, an arylsilyl group having 8 to 40 carbon atoms, a ketoaryl group having 7 to 40 carbon atoms, a halogenated alkyl group having 1 to 40 carbon atoms, and a cyano group, and $R_7$ to $R_8$, $R_8$ to $R_{13}$, and $R_8$ to $R_{12}$ may each independently bind with adjacent substituents to form a saturated or unsaturated ring structure.

4. A material for an organic electroluminescent device represented by the following Chemical Formula 4:

[Chemical Formula 4]

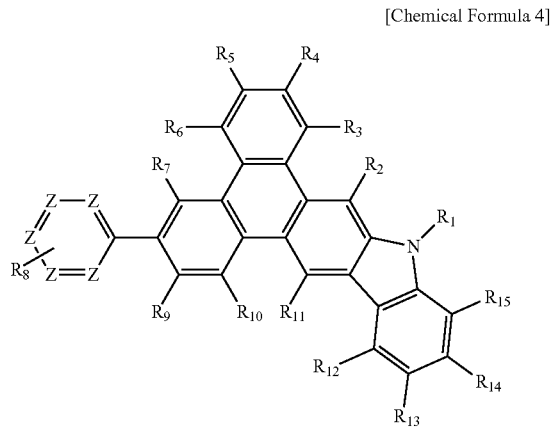

wherein, $R_1$ to $R_{15}$ are each independently selected from the group consisting of hydrogen, deuterium, a halogen atom, an alkyl group having 1 to 40 carbon atoms, a hetero-ring group having 3 to 40 nucleus atoms, an alkoxy group having 1 to 40 carbon atoms, an aromatic hydrocarbon group having 6 to 40 nucleus carbon atoms, an aryloxy group having 6 to 40 carbon atoms, an arylalkyl group having 7 to 40 carbon atoms, an alkenyl group having 2 to 40 carbon atoms, an alkylamino group having 1 to 40 carbon atoms, an arylamino group having 6 to 40 carbon atoms, an arylalkylamino group having 7 to 40 carbon atoms, an alkylsilyl group having 3 to 20 carbon atoms, an arylsilyl group having 8 to 40 carbon atoms, a ketoaryl group having 7 to 40 carbon atoms, a halogenated alkyl group having 1 to 40 carbon atoms, and a cyano group, and a plurality of Zs are each independent and may be the same as or different from each other even though the plurality of Zs are identically represented, and at least one of the plurality of Zs is a nitrogen atom and others are a carbon atom.

5. An organic light emitting device comprising:
an anode;
a cathode; and
one or more organic layers interposed between the anode and the cathode,
wherein at least one of the organic layers comprises one or more compounds selected from the group consisting of a compound represented by the following Chemical Formula 1, a compound represented by the following Chemical Formula 2, a compound represented by the following Chemical Formula 3, and a compound represented by the following Chemical Formula 4:

[Chemical Formula 1]

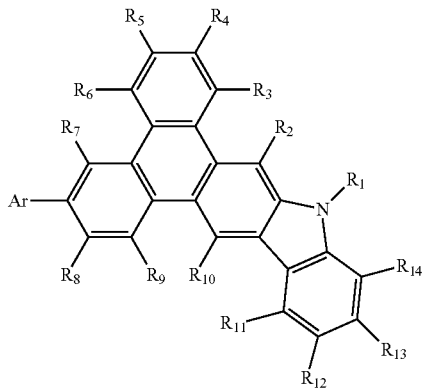

wherein,
Ar is an aromatic hydrocarbon ring group or an aromatic amine ring group, and selected from the group consisting of benzene, naphthalene, biphenyl, anthracene, phenanthrene, pyrene, perylene, triphenylene, and triphenyl amine;
$R_1$ to $R_{14}$ are each independently selected from the group consisting of hydrogen, deuterium, a halogen atom, an alkyl group having 1 to 40 carbon atoms, a hetero-ring group having 3 to 40 nucleus atoms, an alkoxy group having 1 to 40 carbon atoms, an aromatic hydrocarbon group having 6 to 40 nucleus carbon atoms, an aryloxy group having 6 to 40 carbon atoms, an arylalkyl group having 7 to 40 carbon atoms, an alkenyl group having 2 to 40 carbon atoms, an alkylamino group having 1 to 40 carbon atoms, an arylamino group having 6 to 40 carbon atoms, an arylalkylamino group having 7 to 40 carbon atoms, an alkylsilyl group having 3 to 20 carbon atoms, an arylsilyl group having 8 to 40 carbon atoms, a ketoaryl group having 7 to 40 carbon atoms, a halogenated alkyl group having 1 to 40 carbon atoms, and a cyano group, and $R_1$ to $R_{14}$ may each independently bind with adjacent substituents, or the substituents introduced to Ar may each independently bind with adjacent substituents to form a saturated or unsaturated ring structure;

[Chemical Formula 2]

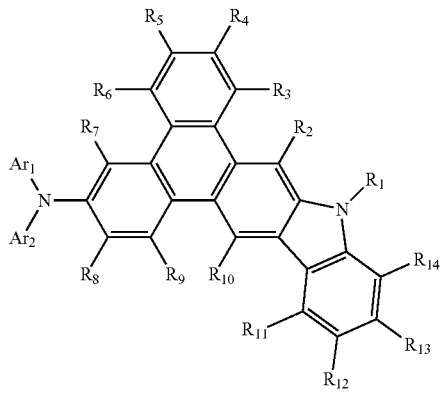

wherein,
$Ar_1$ and $Ar_2$ may be the same as or different from each other, and are each independently selected from the group consisting of benzene, naphthalene, biphenyl, anthracene, phenanthrene, pyrene, perylene, and triphenylene, and $Ar_1$ and $Ar_2$ may each independently bind with the adjacent substituents to form a saturated or unsaturated ring structure,
$R_1$ to $R_{14}$ are the same as definitions of Chemical Formula 1;
$R_1$ to $R_4$, $R_5$ to $R_8$, $R_9$ to $R_{12}$, and $R_{13}$ to $R_{14}$ may each independently bind with adjacent substituents, or $R_{12}$ and $R_{13}$ may be bonded to each other to form a saturated or unsaturated ring structure;

[Chemical Formula 3]

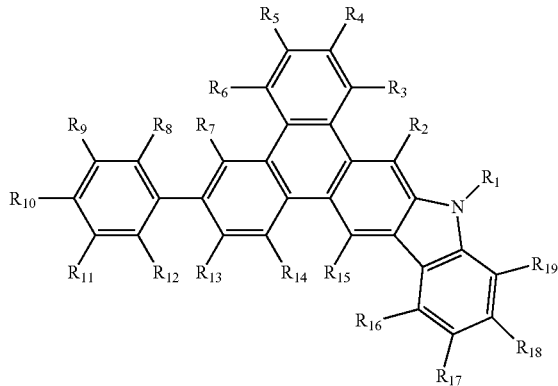

wherein,
$R_1$ to $R_{19}$ are the same as definitions of $R_1$ to $R_{14}$ of Chemical Formula 1;
$R_7$ to $R_8$, $R_8$ to $R_{13}$, and $R_8$ to $R_{12}$ may each independently bind with adjacent substituents to form a saturated or unsaturated ring structure;

[Chemical Formula 4]

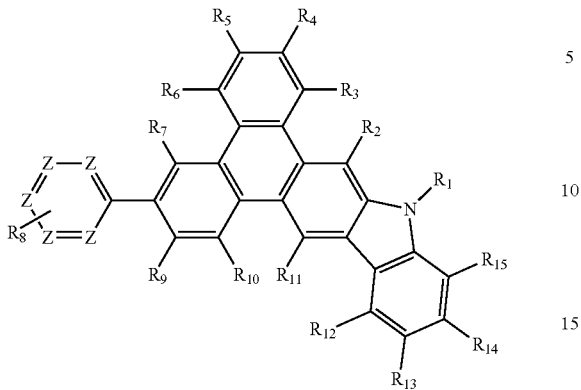

wherein, $R_1$ to $R_{15}$ are the same as definitions of $R_1$ to $R_{14}$ of Chemical Formula 1; and a plurality of Zs are each independent and may be the same as or different from each other even though the plurality of Zs are identically represented, and at least one of the plurality of Zs is a nitrogen atom and others are a carbon atom.

6. The organic light emitting device of claim 5, wherein the compound is included in one or more organic layers selected from the group consisting of a light emitting layer, a hole injection layer, and a hole transport layer.

* * * * *